US006916624B2

(12) United States Patent
Schaefer et al.

(10) Patent No.: US 6,916,624 B2
(45) Date of Patent: Jul. 12, 2005

(54) ANTIBODIES THAT BIND GAMMA-HEREGULIN

(75) Inventors: Gabriele Maria Schaefer, San Francisco, CA (US); Mark Sliwkowski, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 400 days.

(21) Appl. No.: 10/290,578

(22) Filed: Nov. 8, 2002

(65) Prior Publication Data

US 2003/0078389 A1 Apr. 24, 2003

Related U.S. Application Data

(62) Division of application No. 09/514,573, filed on Feb. 28, 2000, now Pat. No. 6,500,941, which is a continuation of application No. 08/891,845, filed on Jul. 10, 1997, now Pat. No. 6,096,873.
(60) Provisional application No. 60/021,640, filed on Jul. 12, 1996, now abandoned.

(51) Int. Cl.[7] .................. G01N 33/53; G01N 33/537; C07K 17/00; C07K 16/00; C12P 21/08

(52) U.S. Cl. .................. 435/7.1; 435/971; 530/399; 530/388.23; 530/389.1; 530/387.1; 530/388.1; 530/389.2

(58) Field of Search ................ 530/397, 399, 530/389.1, 388.23, 387.1, 388.1, 389.2; 435/971, 7.1

(56) References Cited

U.S. PATENT DOCUMENTS

| 4,968,603 A | 11/1990 | Slamon et al. |
| 5,183,884 A | 2/1993 | Kraus et al. |
| 5,367,060 A | 11/1994 | Vandlen et al. |

FOREIGN PATENT DOCUMENTS

| EP | 444961 A1 | 9/1991 |
| EP | 505148 | 9/1992 |
| EP | 0599274 A1 | 6/1994 |
| WO | WO 92/18627 | 10/1992 |
| WO | WO 92/20798 | 11/1992 |
| WO | WO 93/16178 | 8/1993 |
| WO | WO 93/22424 | 11/1993 |
| WO | WO 94/00140 | 1/1994 |
| WO | WO 94/04560 | 3/1994 |
| WO | WO 94/08007 | 4/1994 |
| WO | WO 94/26298 | 11/1994 |
| WO | WO 94/28133 | 12/1994 |
| WO | WO 95/02052 | 1/1995 |
| WO | WO 95/32724 | 7/1995 |
| WO | WO 98/02541 | 1/1998 |

OTHER PUBLICATIONS

Ben–Zur et al, Dev. Biol 217:107–120, (2000).*
Adams et al., "Sequence identification of 2,375 human brain genes" *Nature* 355:632–634 (Feb. 1992).
Beerli et al., "Neu Differentiation Factor Activation of ErbB–3 and ErbB–4 is Cell Specific and Displays a Differential Requirement for ErbB–2" *Molecular & Cellular Biology* 15:6496–6505 (Dec. 1995).
Bowie et al., "Deciphering the Message in Protein Sequences: Tolerance to Amino Acid Substitutions" *Science* 247:1306–1310 (1990).
Brockes et al., "Glial growth factor–like activity in Schwann Cell tumors" *Annals of Neurology* 20:317–322 (1986).
Brockes et al., "Purification and preliminary characterization of a glial growth factor from the bovine pituitary" *Journal of Biological Chemistry* 255(18):8374–8377 (1980).
Brockes, "Assay and isolation of glial growth factor from the bovine pituitary" *Methods in Enzymology* 147:217–225 (1987).
Carraway and Cantley., "A Neu Acquaintance for ErbB3 and ErbB4: A Role for Receptor Heterodimerization in Growth Signaling." *Cell* 78:5–8 (Jul. 15, 1994).
Carraway et al., "The erbB3 gene product is a receptor for heregulin" *Journal of Biological Chemistry* 269(19):14303–14306 (1994).
Chomczynski et al., "Single–step method of RNA isolation by acid guanidinium thiocyanate–phenol–chloroform extraction" *Analytical Biochemistry* 162(1):156–159 (Apr. 1987).
Corfas & Fischbach, "The number of Na$^+$ channels in cultured chick muscle is increased by ARIA, an acetylcholine receptor–inducing activity" *J. Neuroscience* 13(5):2118–2125 (1993).
Danilenko et al., "Neu differentiation factor (NDF) accelerates epidermal migration and differentiation in excisional wounds" *FASEB* 8(4–5):abst No. 3101, p A535 (1994).
Falls et al., "ARIA, a protein that stimulates acetylcholine receptor synthesis, is a member of Neu ligand family" *Cell* 72:801–815 (1993).

(Continued)

*Primary Examiner*—Elizabeth Keimmerer
*Assistant Examiner*—Daniel C. Garnett
(74) *Attorney, Agent, or Firm*—Merchant & Gould P.C.

(57) ABSTRACT

A novel member of the heregulin superfamily has been identified which is designated "γ-HRG". This molecule, secreted by human breast cancer MDA-MB-175 cells, leads to the formation of a constitutive active receptor complex and stimulates the growth of these cells in an autocrine manner. γ-HRG polypeptide and nucleic acid are disclosed, together with various uses therefor (e.g. use of γ-HRG nucleic acid for the recombinant production of γ-HRG). γ-HRG antagonists (e.g. neutralizing antibodies and antisense nucleic acid molecules) as well as uses therefor are also described.

4 Claims, 15 Drawing Sheets

OTHER PUBLICATIONS

Fendly, B.M. et al., "Characterization of Murine Monclonal Antibodies Reactive to Either the Human Epidermal Growth Factor Receptor or HER2/neu Gene Product" *Cancer Research* 50:1550–1558 (Mar. 1, 1990).

Friess et al., "Enhanced erbB–3 Expression in Human Pancreatic Cancer Correlates with Tumor Progression" *Clinical Cancer Research* 1:1413–1420 (1995).

Gorman et al., "Transient Production of Proteins Using an Adenovirus Transformed Cell Line" *DNA Prot. Eng. Tech.* 2(1):3–10 (1990).

Ho, W., et al., "Sensory and Motor Neuron–derived Factor" *Journal of Biological Chemistry* 270(24):14523–14532 (Jun. 16, 1995).

Holmes et al., "Identification of Heregulin, A Specific Activator of p185$^{erbB2}$" *Science* 256:1205–1210 (May 22, 1992).

Huang et al., "Intervening Sequences Increases Efficiency of RNA 3' Processing and Accumulation of Cytoplasmic RNA." *Nucleic Acids Research*, 18(4):937–947 (Feb. 25, 1990).

King et al., "Ligand–independent tyrosine phosphorylation of EGF receptor and the erbB–2/neu proto–oncogene product is induced by hyperosmotic shock" *Oncogene* 4(1):13–18 (Jan. 1989).

Kokai et al., "Synergistic Interaction of p185c–neu and the EGF Receptor Leads to Transformation of Rodent Fibroblasts" *Cell* 58:287–292 (Jul. 28, 1989).

Kozak, "An analysis of 5'–noncoding sequences from 699 vertebrate messenger RNAs" *Nucleic Acids Research* 15(20):8125–8148 (Oct. 26, 1987).

Kraus et al., "Demonstration of ligand–dependent signaling by the erbB–3 tyrosine kinase and its constitutive activation in human breast tumor cells," *Proc. Natl. Acad. Sci.* 90:2900–2904 (1993).

Kraus et al., "Isolation and Characterization of ERBB3, A Third Member of the ERBB/Epidermal Growth Factor Receptor Family: Evidence for Overexpression in a Subset of Human Mammary Tumors" *Proc. Natl. Acid Sci. USA* 86:9193–9197 (Dec. 1989).

Kung et al., "Isolation of a heregulin–like growth factor secreted by estrogen receptor–negative MDA–MB–231 human breast cancer cells that stimulates estrogen receptor-positive cells" *Biochem. & Biophys. Res. Commun.* 202(3):1357–1365 (Aug. 15, 1994).

Kunkel, T., "Rapid and Efficient Site–Specific Mutagenesis Without Phenotypic Selection" *Proc. Natl. Acad. Sci.* 82:488–492 (1985).

LaVallie et al., "A thioredoxin gene fusion expression system that circumvents inclusion body formation in the *E. coli* cytoplasm" *Bio/Technology* 11(2):187–193 (Feb. 1993).

Lemke & Brockes, "Identification and purification of glial growth factor" *J. Neurosci.* 4(1):75–83 (1984).

Lemoine et al., "Expression of the ERBB3 gene product in breast cancer" *Br. J. Cancer* 66:1116–1121 (1992).

Lemoine et al., "The erbB–3 gene in human pancreatic cancer" *J. Pathol.* 168:269–273 (1993).

Levi et al., "The functional characteristics of Schwann Cells cultured from human peripheral nerve after transplantation into a gap within the rat sciatic nerve" *J. Neuroscience* 14(3):1309–1319 (1994).

Lewis et al., "Differential Response of Human Tumor Cell Lines to Anti–p185$^{HER2}$ Monoclonal Antibodies." *Cancer Immunol. Immunother*. 37:255–263 (1993).

Li et al., "Identification of Gas6 as a Growth Factor for Human Schwann Cells" *The Journal of Neuroscience* 16(6):2012–2019 (Mar. 15, 1996).

Liu et al., "γ–Heregulin: a fusion gene of DOC–4 and neuregulin–1 derived from a chromosome translocation" *Oncogene* 18:7110–7114 (1999).

Marchionni et al., "Glial growth factors are alternatively spliced erbB2 ligand expressed in the nervous system" *Nature* 362:312–318 (1993).

Meyer & Birchmeier, "Distinct isoforms of neuregulin are expressed in mesenchymal and neuronal cells during mouse development" *Proc. Natl. Acad. Sci.* 91:1064–1068 (1994).

Orr–Urtreger et al., "Neural expression and chromosomal mapping of Neu differentiation factor to 8p12–p21" *Proc. Natl. Acad. Sci. USA* 90:1867–1871 (1993).

Peles et al., "Cell–type specific interaction of Neu differentiation factor (NDF/heregulin) with Neu/HER–2 suggests complex ligand–receptor relationships" *EMBO Journal* 12(3):961–971 (1993).

Peles et al., "Isolation of the Neu/HER–2 Stimulatory Ligand: A 44 Kd Glycoprotein that Induces Differentiation of Mammary Tumor Cells" *Cell* 69(1):205–216 (1992).

Pinkas–Kramarski et al., "Brain neurons and glial cells express Neu differentiation factor/heregulin: A survival factor for astrocytes" *Proc. Natl. Acad. Sci. USA* 91:9387–9391 (1994).

Plowman et al., "Heregulin Induces Tyrosine Phosphorylation of HER4/p180$^{erbB4}$" *Nature* (Letters to Nature) 366:473–475 (Dec. 2, 1993).

Plowman et al., "Ligand–Specific Activation of HER4/p180$^{erbB4}$, A Fourth Member of the Epidermal Growth Factor Receptor Family" *Proc. Natl. Acad. Sci. USA* 90:1746–1750 (Mar. 1993).

Poller et al., "Production and characterization of a polyclonal antibody to the c–erbB–3 protein: examination of c–erbB–3 protein expression in adenocarcinomas" *J. Pathol.* 168(3):275–280 (1992).

Rajkumar et al., "Expression of the c–erbB–3 protein in gastrointestinal tract tumors determined by monoclonal antibody RTJ1" *J. Pathol.* (Published erratum appears in J.Pathol.Oct. 1993;171(2):154) 170:271–278 (1993).

Sambrook et al. *Molecular Cloning* pp. 16.3–16.22 (1989).

Sambrook et al. *Molecular Cloning: A Laboratory Manual*, Second edition, New York:Cold Spring Harbor Laboratory Press (1989).

Sanidas et al., "Expression of the c–erbB–3 gene product in gastric cancer" *Int. J. Cancer* 54:935–940 (1993).

Schaefer et al., "γ–Heregulin: A Novel Heregulin Isoform That is an Autocrine Growth Factor for the Human Breast Cancer Cell Line, MDA–MB–175" *Oncogene* 15:1385–1394 (1997).

Sklar et al., "A novel growth factor for muscle–rhGGF2" *J. Cell Biochem.* (abstract w642) pp. 540 (1994).

Slamon et al., "Human Breast Cancer: Correlation of Relapse and Survival with Amplification of the HER–2/neu Oncogene" *Science* 235:177–182 (Jan. 9, 1987).

Slamon et al., "Studies of the HER–2/neu Proto–Oncogene in Human Breast and Ovarian Cancer" *Science* 244:707–712 (May 12, 1989).

Sliwkowski et al., "Coexpression of a erbB2 and erbB3 Proteins Reconstitutes a High Affinity Receptor for Heregulin" *Journal of Biological Chemistry* 269(20):14661–14665 (May 20, 1994).

Stern and Kamps., "EGF–Stimulated Tyrosine Phosphorylation of p185$^{neu}$: A Potential Model For Receptor Interactions." *EMBO Journal* 7(4):995–1001 (1988).

Wada et al., "Intermolecular Association of the p185$^{neu}$ Protein and EGF Receptor Modulates EGF Receptor Function" *Cell* 61:1339–1347 (Jun. 29, 1990).

Wang et al., "y–heregulin is the product of a chromosomal translocation fusing the DOC4 and HGL/NRG1 genes in the MDA–MB–175 breast cancer cell line" *Oncogene* 18:5718–5721 (1999).

Wells, J. A., "Additivity of Mutational Effects in Proteins" *Biochemistry* 29(37):8509–8517 (Sep. 18, 1990).

Wen et al., "Neu differentiation factor: a transmembrane glycoprotein containing an EGF Domain and an Immunoglobulin Homology Unit" *Cell* 69(3):559–572 (1992).

Wen et al., "Structural and functional aspects of the multiplicity of neu differentiation factors" *Molecular & Cellular Biology* 14(3):1909–1919 (1994).

* cited by examiner

```
  1 GGGTACCATGGGTCGGTGAGCGCGTTTCCCGCCTGAGCGCAACTAGCGGC
 51 GGGTCGTGGGCACCTCCAGAAAAGATCCCGCACCATCCTCCAGGATCCAA
101 TGGCCTTGGAGAGAGGGCTGCAGGGCCCACGGACATTGCTGACTCTTCAG
151 AACGTGCTGACATGGAGCCAGGTAGACTGAAATTATCATGTGTCCAAATT
201 AAAATTGCATACTTCAAGGATTATTTGAAGGACTATTCTTAGACCCTTTT
251 AAGAAGATTTAAAGAAAAACCACTCGGCCCTGAGTGCGGCGAGGACCCTG

301 TTTGTGGATGTGGAGGAGCGCGGGCCGGAGGCCATGGACGTGAAGGAGAG
  1                                    M  D  V  K  E  R

351 GAAGCCTTACCGCTCGCTGACCCGGCGCCGCGACGCCGAGCGCCGCTACA
  7  K  P  Y  R  S  L  T  R  R  R  D  A  E  R  R  Y  T

401 CCAGCTCGTCCGCGGACAGCGAGGAGGGCAAAGCCCCGCAGAAATCGTAC
 24  S  S  S  A  D  S  E  E  G  K  A  P  Q  K  S  Y

451 AGCTCCAGCGAGACCCTGAAGGCCTACGACCAGGACGCCCGCCTAGCCTA
 40  S  S  S  E  T  L  K  A  Y  D  Q  D  A  R  L  A  Y

501 TGGCAGCCGCGTCAAGGACATTGTGCCGCAGGAGGCCGAGGAATTCTGCC
 57  G  S  R  V  K  D  I  V  P  Q  E  A  E  E  F  C  R

551 GCACAGGTGCCAACTTCACCCTGCGGGAGCTGGGGCTGGAAGAAGTAACG
 74  T  G  A  N  F  T  L  R  E  L  G  L  E  E  V  T

601 CCCCCTCACGGGACCCTGTACCGGACAGACATTGGCCTCCCCCACTGCGG
 90  P  P  H  G  T  L  Y  R  T  D  I  G  L  P  H  C  G

651 CTACTCCATGGGGGCTGGCTCTGATGCCGACATGGAGGCTGACACGGTGC
107  Y  S  M  G  A  G  S  D  A  D  M  E  A  D  T  V  L

701 TGTCCCCTGAGCACCCCGTGCGTCTGTGGGGCCGGAGCACACGGTCAGGG
124    S  P  E  H  P  V  R  L  W  G  R  S  T  R  S  G

751 CGCAGCTCCTGCCTGTCCAGCCGGGCCAATTCCAATCTCACACTCACCGA
140  R  S  S  C  L  S  S  R  A  N  S  N  L  T  L  T  D

801 CACCGAGCATGAAAACACTGAGACTGATCATCCGGGCGGCCTGCAGAACC
157  T  E  H  E  N  T  E  T  D  H  P  G  G  L  Q  N  H

851 ACGCGCGGCTCCGGACGCCGCCGCCGCCGCTCTCGCACGCCCACACCCCC
174    A  R  L  R  T  P  P  P  P  L  S  H  A  H  T  P

901 AACCAGCACCACGCGGCCTCCATTAACTCCCTGAACCGGGGCAACTTCAC
190  N  Q  H  H  A  A  S  I  N  S  L  N  R  G  N  F  T

951 GCCGAGGAGCAACCCCAGCCCGGCCCCCACGGACCACTCGCTCTCCGGAG
207  P  R  S  N  P  S  P  A  P  T  D  H  S  L  S  G  E

1001 AGCCCCCTGCCGGCGGCGCCCAGGAGCCTGCCCACGCCCAGGAGAACTGG
 224    P  P  A  G  G  A  Q  E  P  A  H  A  Q  E  N  W

1051 CTGCTCAACAGCAACATCCCCCTGGAGACCAGAAACCTAGGCAAGCAGCC
 240  L  L  N  S  N  I  P  L  E  T  R  N  L  G  K  Q  P
```

FIG._1A

```
1101 ATTCCTAGGGACATTGCAGGACAACCTCATTGAGATGGACATTCTCGGCG
 257  F   L   G   T   L   Q   D   N   L   I   E   M   D   I   L   G   A

1151 CCTCCCGCCATGATGGGGCTTACAGTGACGGGCACTTCCTCTTCAAGCCT
 274   S   R   H   D   G   A   Y   S   D   G   H   F   L   F   K   P

1201 GGAGGCACCTCCCCGCTCTTCTGCACCACATCACCAGGGTACCCACTGAC
 290   G   G   T   S   P   L   F   C   T   T   S   P   G   Y   P   L   T

1251 GTCCAGCACAGTGTACTCTCCTCCGCCCCGACCCCTGCCCCGCAGCACCT
 307   S   S   T   V   Y   S   P   P   P   R   P   L   P   R   S   T   F

1301 TCGCCCGGCCGGCCTTTAACCTCAAGAAGCCCTCCAAGTACTGTAACTGG
 324   A   R   P   A   F   N   L   K   K   P   S   K   Y   C   N   W

1351 AAGTGCGCAGCCCTGAGCGCCATCGTCATCTCAGCCACTCTGGTCATCCT
 340   K   C   A   A   L   S   A   I   V   I   S   A   T   L   V   I   L

1401 GCTGGCATACTTTGTGGCCATGCACCTGTTTGGCCTAAACTGGCACCTGC
 357   L   A   Y   F   V   A   M   H   L   F   G   L   N   W   H   L   Q

1451 AGCCGATGGAGGGGCAGATGTATGAGATCACGGAGGACACAGCCAGCAGT
 374   P   M   E   G   Q   M   Y   E   I   T   E   D   T   A   S   S

1501 TGGCCTGTGCCAACCGACGTCTCCCTATACCCCTCAGGGGGCACTGGCTT
 390   W   P   V   P   T   D   V   S   L   Y   P   S   G   G   T   G   L

1551 AGAGACCCCTGACAGGAAAGGCAAAGGAACCACAGAAGGAAAGCCCAGTA
 407   E   T   P   D   R   K   G   K   G   T   T   E   G   K   P   S   S

1601 GTTTCTTTCCAGAGGACAGTTTCATAGATTCTGGAGAAATTGATGTGGGA
 424   F   F   P   E   D   S   F   I   D   S   G   E   I   D   V   G

1651 AGGCGAGCTTCCCAGAAGATTCCTCCTGGCACTTTCTGGAGATCTCAAGT
 440   R   R   A   S   Q   K   I   P   P   G   T   F   W   R   S   Q   V

1701 GTTCATAGACCATCCTGTGCATCTGAAATTCAATGTGTCTCTGGGAAAGG
 457   F   I   D   H   P   V   H   L   K   F   N   V   S   L   G   K   A

1751 CAGCCCTGGTTGGCATTTATGGCAGAAAAGGCCTCCCTCCTTCACATACA
 474    A   L   V   G   I   Y   G   R   K   G   L   P   P   S   H   T

1801 CAGTTTGACTTTGTGGAGCTGCTGGATGGCAGGAGGCTCCTAACCCAGGA
 490    Q   F   D   F   V   E   L   L   D   G   R   R   L   L   T   Q   E

1851 GGCGCGGAGCCTAGAGGGGACCCCGCGCCAGTCTCGGGGAACTGTGCCCC
 507    A   R   S   L   E   G   T   P   R   Q   S   R   G   T   V   P   P

1901 CCTCCAGCCATGAGACAGGCTTCATCCAGTATTTGGATTCAGGAATCTGG
 524    S   S   H   E   T   G   F   I   Q   Y   L   D   S   G   I   W

1951 CACTTGGCTTTTTACAATGACGGAAAGGAGTCAGAAGTGGTTTCCTTTCT
 540    H   L   A   F   Y   N   D   G   K   E   S   E   V   V   S   F   L
```

FIG. 1B

```
2001 CACCACTGCCATTGCCTTGCCTCCCCGATTGAAAGAGATGAAAAGCCAGG
 557  T  T  A  I  A  L  P  P  R  L  K  E  M  K  S  Q  E

2051 AATCGGCTGCAGGTTCCAAACTAGTCCTTCGGTGTGAAACCAGTTCTGAA
 574    S  A  A  G  S  K  L  V  L  R  C  E  T  S  S  E

2101 TACTCCTCTCTCAGATTCAAGTGGTTCAAGAATGGGAATGAATTGAATCG
 590  Y  S  S  L  R  F  K  W  F  K  N  G  N  E  L  N  R

2151 AAAAAACAAACCACAAAATATCAAGATACAAAAAAAGCCAGGGAAGTCAG
 607  K  N  K  P  Q  N  I  K  I  Q  K  K  P  G  K  S  E

2201 AACTTCGCATTAACAAAGCATCACTGGCTGATTCTGGAGAGTATATGTGC
 624    L  R  I  N  K  A  S  L  A  D  S  G  E  Y  M  C

2251 AAAGTGATCAGCAAATTAGGAAATGACAGTGCCTCTGCCAATATCACCAT
 640  K  V  I  S  K  L  G  N  D  S  A  S  A  N  I  T  I

2301 CGTGGAATCAAACGAGATCATCACTGGTATGCCAGCCTCAACTGAAGGAG
 657  V  E  S  N  E  I  I  T  G  M  P  A  S  T  E  G  A

2351 CATATGTGTCTTCAGAGTCTCCCATTAGAATATCAGTATCCACAGAAGGA
 674    Y  V  S  S  E  S  P  I  R  I  S  V  S  T  E  G

2401 GCAAATACTTCTTCATCTACATCTACATCCACCACTGGGACAAGCCATCT
 690  A  N  T  S  S  S  T  S  T  S  T  T  G  T  S  H  L

2451 TGTAAAATGTGCGGAGAAGGAGAAAACTTTCTGTGTGAATGGAGGGGAGT
 707  V  K  C  A  E  K  E  K  T  F  C  V  N  G  G  E  C

2501 GCTTCATGGTGAAAGACCTTTCAAACCCCTCGAGATACTTGTGCAAGTGC
 724  F  M  V  K  D  L  S  N  P  S  R  Y  L  C  K  C

2551 CCAAATGAGTTTACTGGTGATCGCTGCCAAAACTACGTAATGGCCAGCTT
 740  P  N  E  F  T  G  D  R  C  Q  N  Y  V  M  A  S  F

2601 CTACAGTACGTCCACTCCCTTTCTGTCTCTGCCTGAATAGGAGCATGCTC
 757  Y  S  T  S  T  P  F  L  S  L  P  E

2651 AGTTGGTGCTGCTTTCTTGTTGCTGCATCTCCCCTCAGATTCCACCTAGA

2701 GCTAGATGTGTCTTACCAGATCTAATATTGACTGCCTCTGCCTGTCGCAT
2751 GAGAACATTAACAAAAGCAATTGTATTACTTCCTCTGTTCGCGACTAGTT
2801 GGCTCTGAGATACTAATAGGTGTGTGAGGCTCCGGATGTTTCTGGAATTG
2851 ATATTGAATGATGTGATACAAATTGATAGTCAATATCAAGCAGTGAAATA
2901 TGATAATAAAGGCATTTCAAAGTCTCACTTTTATTGATAAAATAAAAATC
2951 ATTCTACTGAACAGTCCATCTTCTTTATACAATGACCACATCCTGAAAAG
3001 GGTGTTGCTAAGCTGTAACCGATATGCACTTGAAATGATGGTAAGTTAAT
3051 TTTGATTCAGAATGTGTTATTTGTCACAAATAAACATAATAAAAGGAAAA
3101 AAAAAAAAA
```

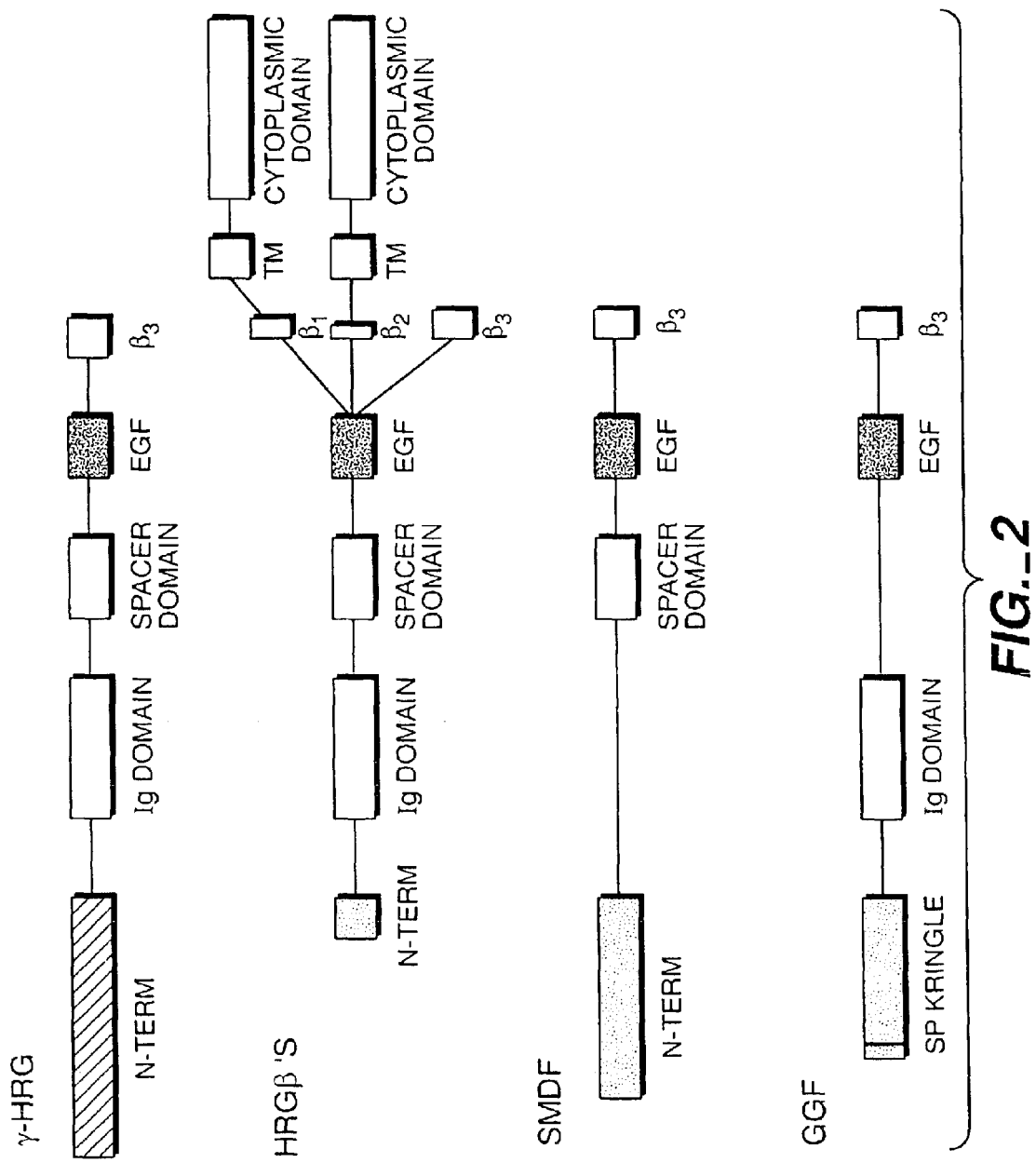
FIG._2

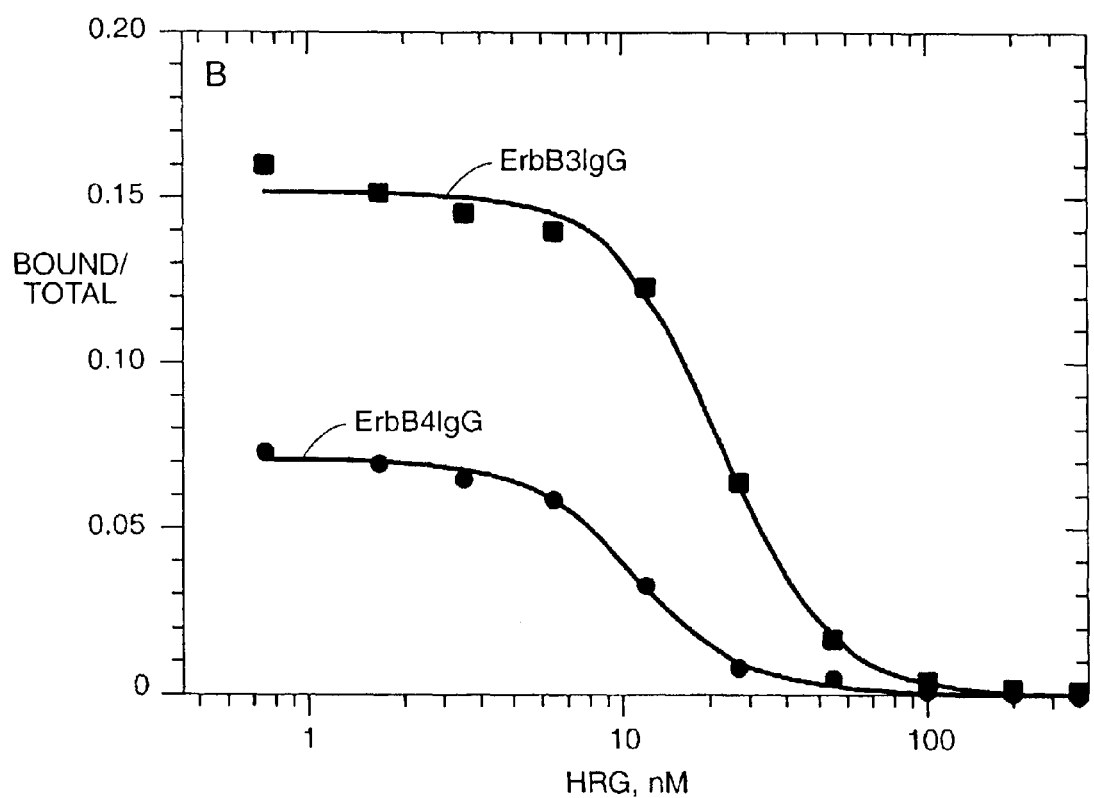
FIG._3

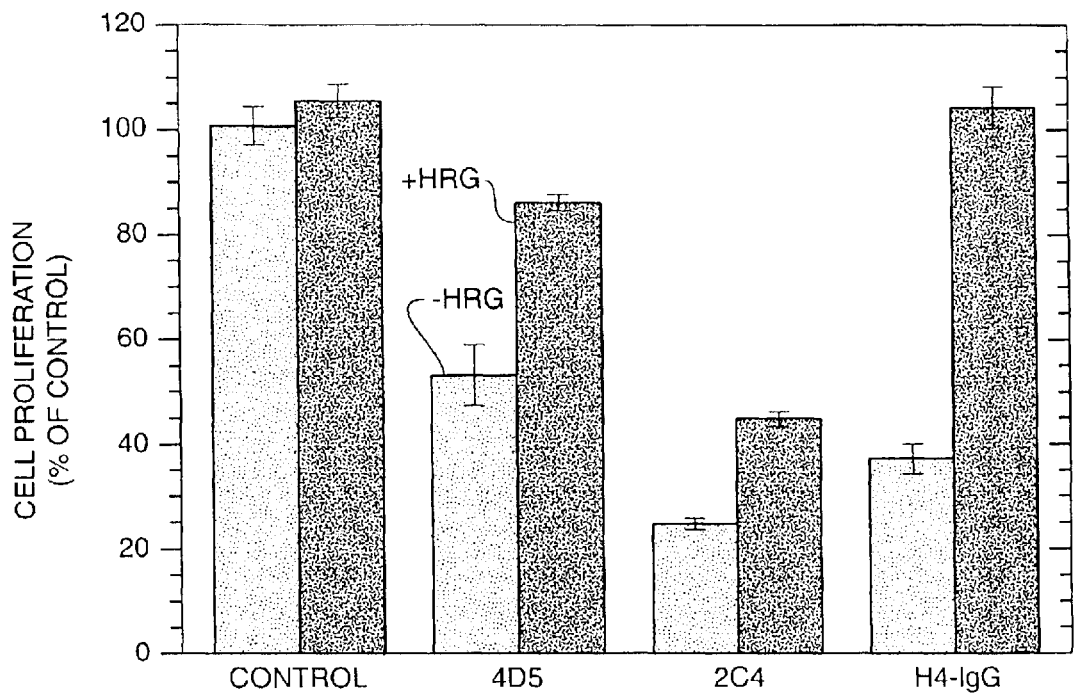
FIG._4A
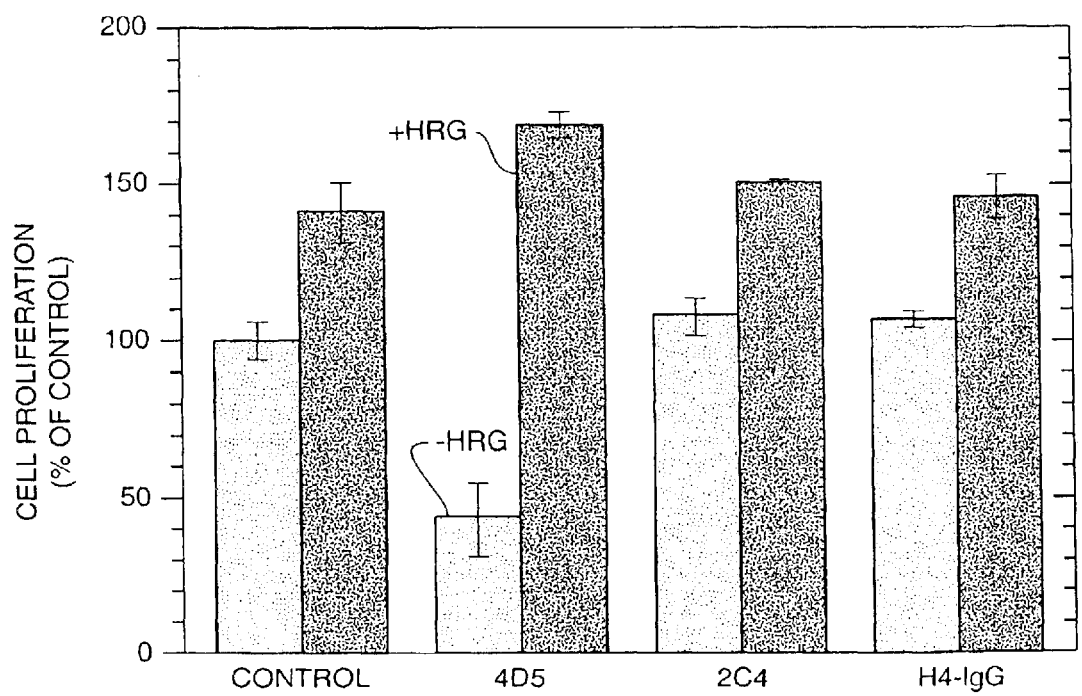
FIG._4B

```
gammaHRG     1 MDVKERKPYRSLTRRRDAERRYTSSSADSEEGKAPQKSYSSSETLKAYDQ gammaHRG    51 DARLAYGSRVKDIVPQEAEEFCRTGANFTLRELGLEEVTPPHGTLYRTDI gammaHRG   101 GLPHCGYSMGAGSDADMEADTVLSPEHPVRLWGRSTRSGRSSCLSSRANS gammaHRG   151 NLTLTDTEHENTETDHPGGLQNHARLRTPPPLSHAHTPNQHHAASINSL gammaHRG   201 NRGNFTPRSNPSPAPTDHSLSGEPPAGGAQEPAHAQENWLLNSNIPLETR gammaHRG   251 NLGKQPFLGTLQDNLIE MDILGASRHDGAYSDGHFLFKPGGTSPLFCTTS
clone20      1                  MDILGASRHDGAYSDGHFLFKPGGTSPLFCTTS gammaHRG   301 PGYPLTSSTVYSPPPRPLPRSTFARPAFNLKKPSKYCNWKCAALSAIVIS
clone20     34 PGYPLTSSTVYSPPPRPLPRSTFARPAFNLKKPSKYCNWKCAALSAIVIS gammaHRG   351 ATLVILLAYFVAMHLFGLNWHLQPMEGQMYEITEDTASSWPVPTDVSLYP
clone20     84 ATLVILLAYFVAMHLFGLNWHLQPMEGQMYEITEDTASSWPVPTDVSLYP gammaHRG   401 SGGTGLETPDRKGKGTTEGKPSSFFPEDSFIDSGEIDVGRRASQKIPPGT
clone20    134 SGGTGLETPDRKGKGTTEGKPSSFFPEDSFIDSGEIDVGRRASQKIPPGT gammaHRG   451 FWRSQVFIDHPVHLKFNVSLGKAALVGIYGRKGLPPSHTQFDFVELLDGR
clone20    184 FWRSQVFIDHPVHLKFNVSLGKAALVGIYGRKGLPPSHTQFDFVELLDGR
```

FIG._5A

```
gammaHRG  501  RLLTQEARSLEGTPRQSRGTVPPSSHETGFIQYLDSGIWHLAFYNDGKES
clone20   234  RLLTQEARSLEGTPRQSRGTVPPSSHETGFIQYLDSGIWHLAFYNDGKES gammaHRG  551  EVVSFLTTAI------------------------ALPPRLKEMKSQES
clone20   284  EVVSFLTTAIDSSGTGQSAHVTVQDSVIFQRRGLESALPPRLKEMKSQES gammaHRG  575  AAGSKLVLRCETSSEYSSLRFKWFKNGNELNRKNKPQNIKIQKKPGKSEL
clone20   334  AAGSKLVLRCETSSEYSSLRFKWFKNGNELNRKNKPQNIKIQKKPGKSEL gammaHRG  625  RINKASLADSGEYMCKVISKLGNDSASANITTIVESNEIITGMPASTEGAY
clone20   384  RINKASLADSGEYMCKVISKLGNDSASANITTIVESNEIITGMPASTEGAY gammaHRG  675  VSSESPIRISVSTEGANTSSSTSTSTTGTSHLVKCAEKEKTFCVNGGECF
clone20   434  VSSESPIRISVSTEGANTSSSTSTSTTGTSHLVKCAEKEKTFCVNGGECF gammaHRG  725  MVKDLSNPSRYLCKCPNEFTGDRCQNYVMASFYSTSTPFLSLPE
clone20   484  MVKDLSNPSRYLCKCPNEFTGDRCQNYVMASFYSTSTPFLSLPE
```

FIG._5B

| FIG._5A |
| FIG._5B |

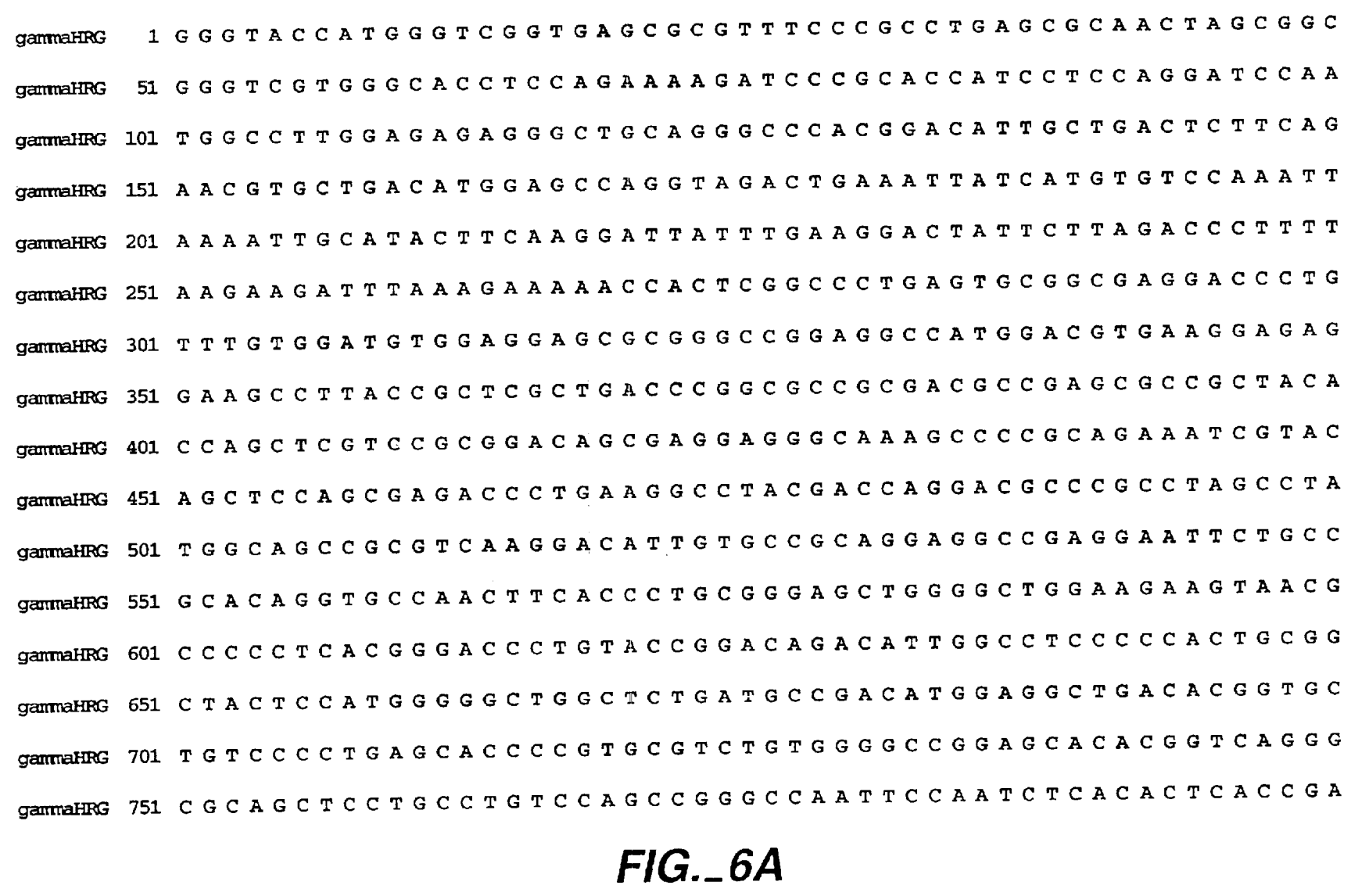

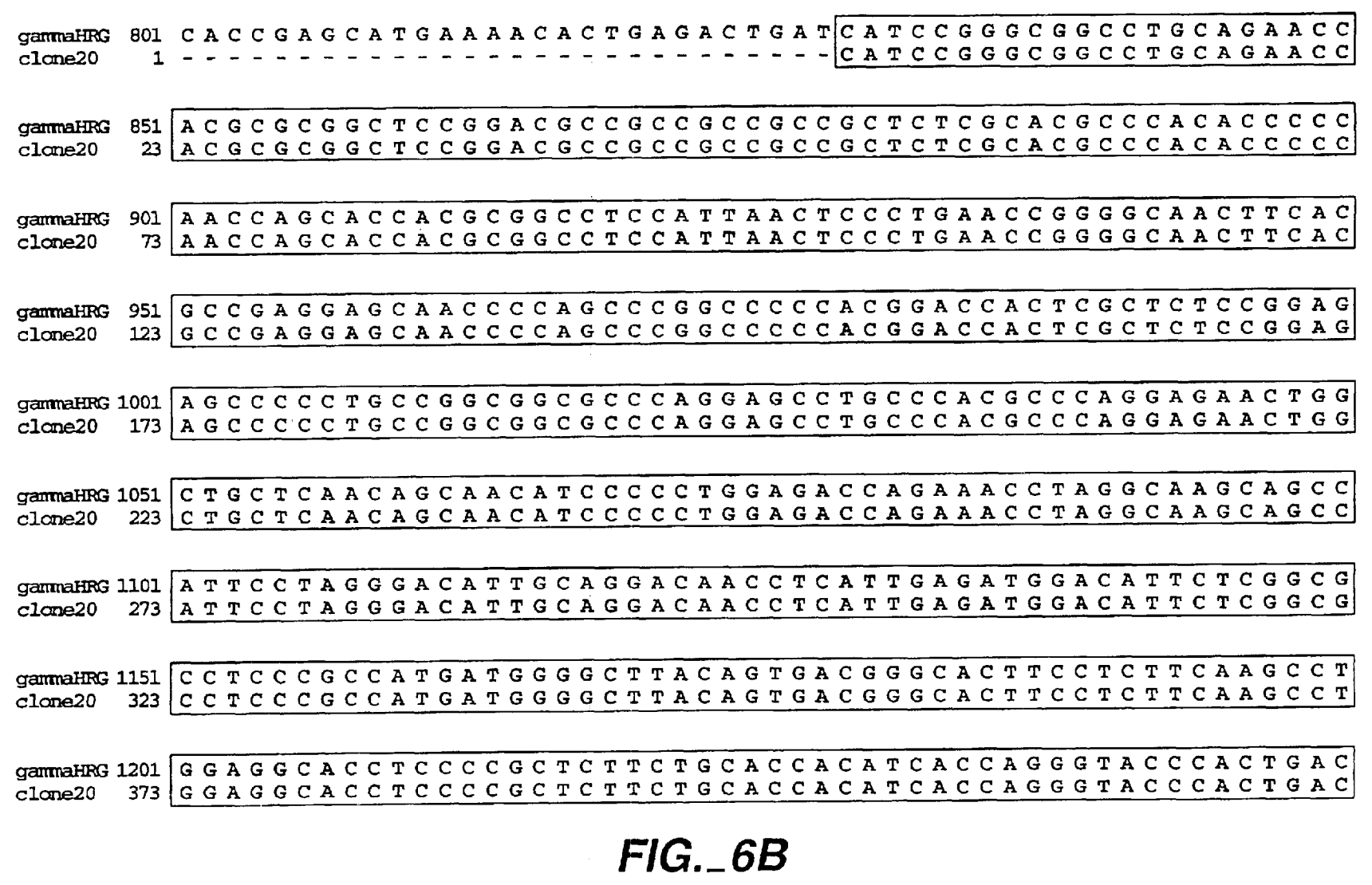

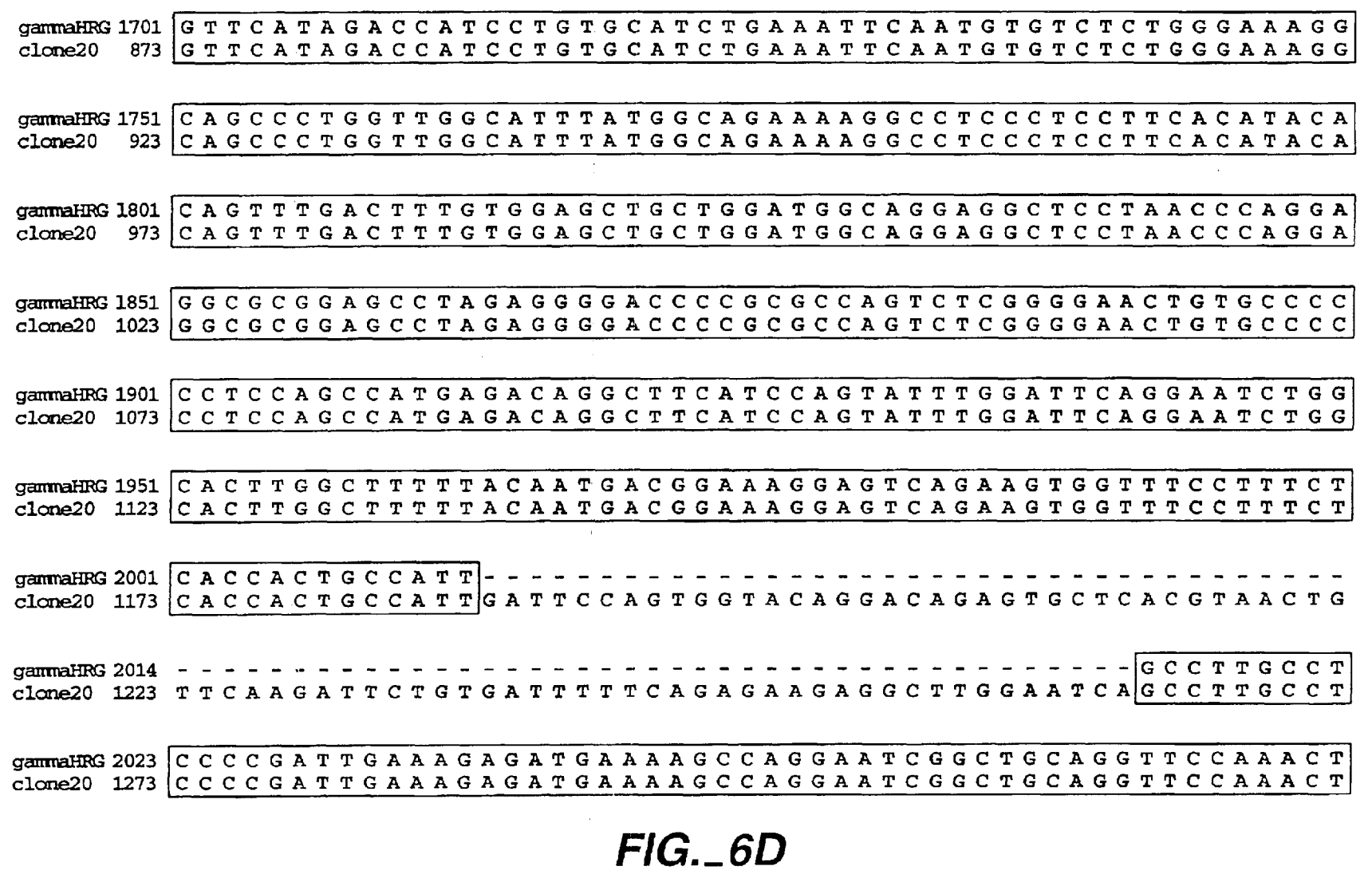

| | | |
|---|---|---|
| gammaHRG | 2073 | AGTCCTTTCGGTGTGAAACCAGTTCTGAAATACTCCTCTCAGATTCAAGT |
| clone20 | 1323 | AGTCCTTTCGGTGTGAAACCAGTTCTGAAATACTCCTCTCAGATTCAAGT |
| gammaHRG | 2123 | GGTTCAAGAATGGGGAATTGAATTGAATCAAACACAAACCAAAAAAATC |
| clone20 | 1373 | GGTTCAAGAATGGGGAATTGAATTGAATCAAACACAAACCAAAAAAATC |
| gammaHRG | 2173 | AAGATACAAAAAAAAGCCAGGGGAAGTCAGAAACTTCGCATTAACAAAGCATC |
| clone20 | 1423 | AAGATACAAAAAAAAGCCAGGGGAAGTCAGAAACTTCGCATTAACAAAGCATC |
| gammaHRG | 2223 | ACTGGCTGATTCTCTGGAGAGTATATGTGCAAAAGTGATCAGCAAAATTAGGAA |
| clone20 | 1473 | ACTGGCTGATTCTCTGGAGAGTATATGTGCAAAAGTGATCAGCAAAATTAGGAA |
| gammaHRG | 2273 | ATGACAGTGCCCTCTGCCCAATATCACCATCATCGTGGAAATCAAAACGAGATCATC |
| clone20 | 1523 | ATGACAGTGCCCTCTGCCCAATATCACCATCATCGTGGAAATCAAAACGAGATCATC |
| gammaHRG | 2323 | ATGGTATGCCCAGCCCTCAAACTGAAAGGAGCCATATGTGTTCTTTCAGTTCCC |
| clone20 | 1573 | ATGGTATGCCCAGCCCTCAAACTGAAAGGAGCCATATGTGTTCTTTCAGTTCCC |
| gammaHRG | 2373 | CATTAGAAATATCAGTAATCCACAGAAGGAGCAACTTTCATCTACAT |
| clone20 | 1623 | CATTAGAAATATCAGTAATCCACAGAAGGAGCAACTTTCATCTACAT |
| gammaHRG | 2423 | CTACATCCACCAAAGCCCAGACAAAGCCATCTTGTAAAAATGGCTTCAAGGAG |
| clone20 | 1673 | CTACATCCACCAAAGCCCAGACAAAGCCATCTTGTAAAAATGGCTTCAAGGAG |
| gammaHRG | 2473 | AAAACTTTCTGTGTGAATGGTGAATGGGAGGGGAGTGCTTCATGAAAGACCTTTC |
| clone20 | 1723 | AAAACTTTCTGTGTGAATGGTGAATGGGAGGGGAGTGCTTCATGAAAGACCTTTC |

```
gammaHRG  2523  AAACCCCTCGAGATACTTGTGCAAGTGCCCAAATGAGTTTACTGGTGATC
clone20   1773  AAACCCCTCGAGATACTTGTGCAAGTGCCCAAATGAGTTTACTGGTGATC gammaHRG  2573  GCTGCCAAAAACTACAGTGGTAATGGCCCAGCCTTCTACAGTACCTCCTTT
clone20   1823  GCTGCCAAAAACTACAGTGGTAATGGCCCAGCCTTCTACAGTACCTCCTTT gammaHRG  2623  CTGTCTCTGCCCCTGAAATAGGAGGAGCATGCCAGTTGGGTGCCTTTTGTT
clone20   1873  CTGTCTCTGCCCCTGAAATAGGAGGAGCATGCCAGTTGGGTGCCTTTTGTT gammaHRG  2673  CTGCATCTCCCCCCCCAGATTCCACCTAGCCAGTGTCTCTTACCAGATT
clone20   1923  CTGCATCTCCCCCCCCAGATTCCACCTAGCCAGTGTCTCTTACCAGATT gammaHRG  2723  TAATATTGACTTCCCTCTGCCCCTGTCGCATGAGAAACATTAACAATT
clone20   1973  TAATATTGACTTCCCTCTGCCCCTGTCGCATGAGAAACATTAACAATT gammaHRG  2773  GTATTACTTTCCCTCTGTTCGGCGACTAGTTGGCTCTGAAATTGAAGCAA
clone20   2023  GTATTACTTTCCCTCTGTTCGGCGACTAGTTGGCTCTGAAATTGAAGCAA gammaHRG  2823  TGTGAGGCTCCCGGCTAGCCAGTTTCTGGAAATATTGATAAATAAATAGGA
clone20   2073  TGTGAGGCTCCCGGCTAGCCAGTTTCTGGAAATATTGATAAATAAATAGGA gammaHRG  2873  TTGATAGTCAAATAATCAAAGCAGCATAAAAGGCATTTCAAA
clone20   2123  TTGATAGTCAAATAATCAAAGCAGCATAAAAGGCATTTCAAA gammaHRG  2923  TCTCACTTTTATTTGATAAAATCATTCTGAACAGTCCATCTT
clone20   2173  TCTCACTTTTATTTGATAAAATCATTCTGAACAGTCCATCTT
```

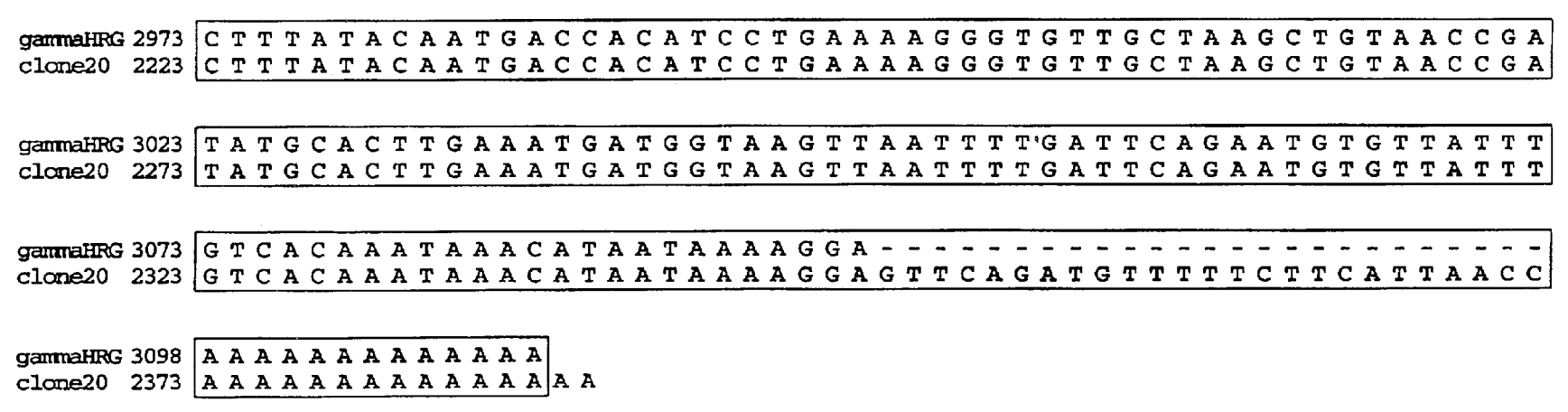

FIG._6G

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 3111 base pairs
      (B) TYPE: Nucleic Acid
      (C) STRANDEDNESS: Single
      (D) TOPOLOGY: Linear (xi) SEQUENCE DESCRIPTION: SEQ ID NO: 1:

```
GGGTACCATG GGTCGGTGAG CGCGTTTCCC GCCTGAGCGC AACTAGCGGC            50

GGGTCGTGGG CACCTCCAGA AAAGATCCCG CACCATCCTC CAGGATCCAA           100

TGGCCTTGGA GAGAGGGCTG CAGGGCCCAC GGACATTGCT GACTCTTCAG           150

AACGTGCTGA CATGGAGCCA GGTAGACTGA AATTATCATG TGTCCAAATT           200

AAAATTGCAT ACTTCAAGGA TTATTTGAAG GACTATTCTT AGACCCTTTT           250
```

-continued

| | |
|---|---|
| AAGAAGATTT AAAGAAAAAC CACTCGGCCC TGAGTGCGGC GAGGACCCTG | 300 |
| TTTGTGGATG TGGAGGAGCG CGGGCCGGAG GCCATGGACG TGAAGGAGAG | 350 |
| GAAGCCTTAC CGCTCGCTGA CCCGGCGCCG CGACGCCGAG CGCCGCTACA | 400 |
| CCAGCTCGTC CGCGGACAGC GAGGAGGGCA AAGCCCCGCA GAAATCGTAC | 450 |
| AGCTCCAGCG AGACCCTGAA GGCCTACGAC CAGGACGCCC GCCTAGCCTA | 500 |
| TGGCAGCCGC GTCAAGGACA TTGTGCCGCA GGAGGCCGAG GAATTCTGCC | 550 |
| GCACAGGTGC CAACTTCACC CTGCGGGAGC TGGGGCTGGA AGAAGTAACG | 600 |
| CCCCCTCACG GGACCCTGTA CCGGACAGAC ATTGGCCTCC CCCACTGCGG | 650 |
| CTACTCCATG GGGGCTGGCT CTGATGCCGA CATGGAGGCT GACACGGTGC | 700 |
| TGTCCCCTGA GCACCCCGTG CGTCTGTGGG GCCGGAGCAC ACGGTCAGGG | 750 |
| CGCAGCTCCT GCCTGTCCAG CCGGGCCAAT TCCAATCTCA CACTCACCGA | 800 |
| CACCGAGCAT GAAAACACTG AGACTGATCA TCCGGGCGGC CTGCAGAACC | 850 |
| ACGCGCGGCT CCGGACGCCG CCGCCGCCGC TCTCGCACGC CCACACCCCC | 900 |
| AACCAGCACC ACGCGGCCTC CATTAACTCC CTGAACCGGG GCAACTTCAC | 950 |
| GCCGAGGAGC AACCCCAGCC CGGCCCCCAC GGACCACTCG CTCTCCGGAG | 1000 |
| AGCCCCCTGC CGGCGGCGCC CAGGAGCCTG CCCACGCCCA GGAGAACTGG | 1050 |
| CTGCTCAACA GCAACATCCC CCTGGAGACC AGAAACCTAG GCAAGCAGCC | 1100 |
| ATTCCTAGGG ACATTGCAGG ACAACCTCAT TGAGATGGAC ATTCTCGGCG | 1150 |
| CCTCCCGCCA TGATGGGGCT TACAGTGACG GGCACTTCCT CTTCAAGCCT | 1200 |
| GGAGGCACCT CCCCGCTCTT CTGCACCACA TCACCAGGGT ACCCACTGAC | 1250 |
| GTCCAGCACA GTGTACTCTC CTCCGCCCCG ACCCCTGCCC CGCAGCACCT | 1300 |
| TCGCCCGGCC GGCCTTTAAC CTCAAGAAGC CCTCCAAGTA CTGTAACTGG | 1350 |
| AAGTGCGCAG CCCTGAGCGC CATCGTCATC TCAGCCACTC TGGTCATCCT | 1400 |
| GCTGGCATAC TTTGTGGCCA TGCACCTGTT TGGCCTAAAC TGGCACCTGC | 1450 |
| AGCCGATGGA GGGGCAGATG TATGAGATCA CGGAGGACAC AGCCAGCAGT | 1500 |
| TGGCCTGTGC CAACCGACGT CTCCCTATAC CCCTCAGGGG GCACTGGCTT | 1550 |
| AGAGACCCCT GACAGGAAAG GCAAAGGAAC CACAGAAGGA AAGCCCAGTA | 1600 |
| GTTTCTTTCC AGAGGACAGT TTCATAGATT CTGGAGAAAT TGATGTGGGA | 1650 |
| AGGCGAGCTT CCCAGAAGAT TCCTCCTGGC ACTTTCTGGA GATCTCAAGT | 1700 |
| GTTCATAGAC CATCCTGTGC ATCTGAAATT CAATGTGTCT CTGGGAAAGG | 1750 |
| CAGCCCTGGT TGGCATTTAT GGCAGAAAAG GCCTCCCTCC TTCACATACA | 1800 |
| CAGTTTGACT TTGTGGAGCT GCTGGATGGC AGGAGGCTCC TAACCCAGGA | 1850 |
| GGCGCGGAGC CTAGAGGGGA CCCCGCGCCA GTCTCGGGGA ACTGTGCCCC | 1900 |
| CCTCCAGCCA TGAGACAGGC TTCATCCAGT ATTTGGATTC AGGAATCTGG | 1950 |
| CACTTGGCTT TTTACAATGA CGGAAAGGAG TCAGAAGTGG TTTCCTTTCT | 2000 |
| CACCACTGCC ATTGCCTTGC CTCCCCGATT GAAAGAGATG AAAAGCCAGG | 2050 |
| AATCGGCTGC AGGTTCCAAA CTAGTCCTTC GGTGTGAAAC CAGTTCTGAA | 2100 |
| TACTCCTCTC TCAGATTCAA GTGGTTCAAG AATGGGAATG AATTGAATCG | 2150 |
| AAAAAACAAA CCACAAAATA TCAAGATACA AAAAAAGCCA GGGAAGTCAG | 2200 |

-continued

| | |
|---|---|
| AACTTCGCAT TAACAAAGCA TCACTGGCTG ATTCTGGAGA GTATATGTGC | 2250 |
| AAAGTGATCA GCAAATTAGG AAATGACAGT GCCTCTGCCA ATATCACCAT | 2300 |
| CGTGGAATCA AACGAGATCA TCACTGGTAT GCCAGCCTCA ACTGAAGGAG | 2350 |
| CATATGTGTC TTCAGAGTCT CCCATTAGAA TATCAGTATC CACAGAAGGA | 2400 |
| GCAAATACTT CTTCATCTAC ATCTACATCC ACCACTGGGA CAAGCCATCT | 2450 |
| TGTAAAATGT GCGGAGAAGG AGAAAACTTT CTGTGTGAAT GGAGGGGAGT | 2500 |
| GCTTCATGGT GAAAGACCTT TCAAACCCCT CGAGATACTT GTGCAAGTGC | 2550 |
| CCAAATGAGT TTACTGGTGA TCGCTGCCAA AACTACGTAA TGGCCAGCTT | 2600 |
| CTACAGTACG TCCACTCCCT TTCTGTCTCT GCCTGAATAG GAGCATGCTC | 2650 |
| AGTTGGTGCT GCTTTCTTGT TGCTGCATCT CCCCTCAGAT TCCACCTAGA | 2700 |
| GCTAGATGTG TCTTACCAGA TCTAATATTG ACTGCCTCTG CCTGTCGCAT | 2750 |
| GAGAACATTA ACAAAAGCAA TTGTATTACT TCCTCTGTTC GCGACTAGTT | 2800 |
| GGCTCTGAGA TACTAATAGG TGTGTGAGGC TCCGGATGTT TCTGGAATTG | 2850 |
| ATATTGAATG ATGTGATACA AATTGATAGT CAATATCAAG CAGTGAAATA | 2900 |
| TGATAATAAA GGCATTTCAA AGTCTCACTT TTATTGATAA AATAAAAATC | 2950 |
| ATTCTACTGA ACAGTCCATC TTCTTTATAC AATGACCACA TCCTGAAAAG | 3000 |
| GGTGTTGCTA AGCTGTAACC GATATGCACT TGAAATGATG GTAAGTTAAT | 3050 |
| TTTGATTCAG AATGTGTTAT TTGTCACAAA TAAACATAAT AAAAGGAAAA | 3100 |
| AAAAAAAAA A | 3111 |

(2) INFORMATION FOR SEQ ID NO: 2:

(i) SEQUENCE CHARACTERISTICS:
        (A) LENGTH: 768 amino acids
        (B) TYPE: Amino Acid
        (D) TOPOLOGY: Linear (xi) SEQUENCE DESCRIPTION: SEQ ID NO: 2:

```
Met Asp Val Lys Glu Arg Lys Pro Tyr Arg Ser Leu Thr Arg Arg
 1               5                  10                  15

Arg Asp Ala Glu Arg Arg Tyr Thr Ser Ser Ala Asp Ser Glu
                20                  25                  30

Glu Gly Lys Ala Pro Gln Lys Ser Tyr Ser Ser Glu Thr Leu
                35                  40                  45

Lys Ala Tyr Asp Gln Asp Ala Arg Leu Ala Tyr Gly Ser Arg Val
                50                  55                  60

Lys Asp Ile Val Pro Gln Glu Ala Glu Glu Phe Cys Arg Thr Gly
                65                  70                  75

Ala Asn Phe Thr Leu Arg Glu Leu Gly Leu Glu Glu Val Thr Pro
                80                  85                  90

Pro His Gly Thr Leu Tyr Arg Thr Asp Ile Gly Leu Pro His Cys
                95                 100                 105

Gly Tyr Ser Met Gly Ala Gly Ser Asp Ala Asp Met Glu Ala Asp
                110                115                 120

Thr Val Leu Ser Pro Glu His Pro Val Arg Leu Trp Gly Arg Ser
                125                130                 135

Thr Arg Ser Gly Arg Ser Ser Cys Leu Ser Ser Arg Ala Asn Ser
                140                145                 150

Asn Leu Thr Leu Thr Asp Thr Glu His Glu Asn Thr Glu Thr Asp
```

-continued

```
                155                 160                 165
His Pro Gly Gly Leu Gln Asn His Ala Arg Leu Arg Thr Pro Pro
            170                 175                 180
Pro Pro Leu Ser His Ala His Thr Pro Asn Gln His His Ala Ala
            185                 190                 195
Ser Ile Asn Ser Leu Asn Arg Gly Asn Phe Thr Pro Arg Ser Asn
            200                 205                 210
Pro Ser Pro Ala Pro Thr Asp His Ser Leu Ser Gly Glu Pro Pro
            215                 220                 225
Ala Gly Gly Ala Gln Glu Pro Ala His Ala Gln Glu Asn Trp Leu
            230                 235                 240
Leu Asn Ser Asn Ile Pro Leu Glu Thr Arg Asn Leu Gly Lys Gln
            245                 250                 255
Pro Phe Leu Gly Thr Leu Gln Asp Asn Leu Ile Glu Met Asp Ile
            260                 265                 270
Leu Gly Ala Ser Arg His Asp Gly Ala Tyr Ser Asp Gly His Phe
            275                 280                 285
Leu Phe Lys Pro Gly Gly Thr Ser Pro Leu Phe Cys Thr Thr Ser
            290                 295                 300
Pro Gly Tyr Pro Leu Thr Ser Ser Thr Val Tyr Ser Pro Pro
            305                 310                 315
Arg Pro Leu Pro Arg Ser Thr Phe Ala Arg Pro Ala Phe Asn Leu
            320                 325                 330
Lys Lys Pro Ser Lys Tyr Cys Asn Trp Lys Cys Ala Ala Leu Ser
            335                 340                 345
Ala Ile Val Ile Ser Ala Thr Leu Val Ile Leu Ala Tyr Phe
            350                 355                 360
Val Ala Met His Leu Phe Gly Leu Asn Trp His Leu Gln Pro Met
            365                 370                 375
Glu Gly Gln Met Tyr Glu Ile Thr Glu Asp Thr Ala Ser Ser Trp
            380                 385                 390
Pro Val Pro Thr Asp Val Ser Leu Tyr Pro Ser Gly Gly Thr Gly
            395                 400                 405
Leu Glu Thr Pro Asp Arg Lys Gly Lys Gly Thr Thr Glu Gly Lys
            410                 415                 420
Pro Ser Ser Phe Phe Pro Glu Asp Ser Phe Ile Asp Ser Gly Glu
            425                 430                 435
Ile Asp Val Gly Arg Arg Ala Ser Gln Lys Ile Pro Pro Gly Thr
            440                 445                 450
Phe Trp Arg Ser Gln Val Phe Ile Asp His Pro Val His Leu Lys
            455                 460                 465
Phe Asn Val Ser Leu Gly Lys Ala Ala Leu Val Gly Ile Tyr Gly
            470                 475                 480
Arg Lys Gly Leu Pro Pro Ser His Thr Gln Phe Asp Phe Val Glu
            485                 490                 495
Leu Leu Asp Gly Arg Arg Leu Leu Thr Gln Glu Ala Arg Ser Leu
            500                 505                 510
Glu Gly Thr Pro Arg Gln Ser Arg Gly Thr Val Pro Pro Ser Ser
            515                 520                 525
His Glu Thr Gly Phe Ile Gln Tyr Leu Asp Ser Gly Ile Trp His
            530                 535                 540
Leu Ala Phe Tyr Asn Asp Gly Lys Glu Ser Glu Val Val Ser Phe
            545                 550                 555
```

```
Leu Thr Thr Ala Ile Ala Leu Pro Pro Arg Leu Lys Glu Met Lys
            560                 565                 570

Ser Gln Glu Ser Ala Ala Gly Ser Lys Leu Val Leu Arg Cys Glu
            575                 580                 585

Thr Ser Ser Glu Tyr Ser Ser Leu Arg Phe Lys Trp Phe Lys Asn
            590                 595                 600

Gly Asn Glu Leu Asn Arg Lys Asn Lys Pro Gln Asn Ile Lys Ile
            605                 610                 615

Gln Lys Lys Pro Gly Lys Ser Glu Leu Arg Ile Asn Lys Ala Ser
            620                 625                 630

Leu Ala Asp Ser Gly Glu Tyr Met Cys Lys Val Ile Ser Lys Leu
            635                 640                 645

Gly Asn Asp Ser Ala Ser Ala Asn Ile Thr Ile Val Glu Ser Asn
            650                 655                 660

Glu Ile Ile Thr Gly Met Pro Ala Ser Thr Glu Gly Ala Tyr Val
            665                 670                 675

Ser Ser Glu Ser Pro Ile Arg Ile Ser Val Ser Thr Glu Gly Ala
            680                 685                 690

Asn Thr Ser Ser Ser Thr Ser Thr Ser Thr Thr Gly Thr Ser His
            695                 700                 705

Leu Val Lys Cys Ala Glu Lys Glu Lys Thr Phe Cys Val Asn Gly
            710                 715                 720

Gly Glu Cys Phe Met Val Lys Asp Leu Ser Asn Pro Ser Arg Tyr
            725                 730                 735

Leu Cys Lys Cys Pro Asn Glu Phe Thr Gly Asp Arg Cys Gln Asn
            740                 745                 750

Tyr Val Met Ala Ser Phe Tyr Ser Thr Ser Thr Pro Phe Leu Ser
            755                 760                 765

Leu Pro Glu
      768

(2) INFORMATION FOR SEQ ID NO: 3:

(i) SEQUENCE CHARACTERISTICS:
        (A) LENGTH: 1680 base pairs
        (B) TYPE: Nucleic Acid
        (C) STRANDEDNESS: Single
        (D) TOPOLOGY: Linear (xi) SEQUENCE DESCRIPTION: SEQ ID NO: 3:

ATGGACGTGA AGGAGAGGAA GCCTTACCGC TCGCTGACCC GGCGCCGCGA         50

CGCCGAGCGC CGCTACACCA GCTCGTCCGC GGACAGCGAG GAGGGCAAAG        100

CCCCGCAGAA ATCGTACAGC TCCAGCGAGA CCCTGAAGGC CTACGACCAG        150

GACGCCCGCC TAGCCTATGG CAGCCGCGTC AAGGACATTG TGCCGCAGGA        200

GGCCGAGGAA TTCTGCCGCA CAGGTGCCAA CTTCACCCTG CGGGAGCTGG        250

GGCTGGAAGA AGTAACGCCC CCTCACGGGA CCCTGTACCG GACAGACATT        300

GGCCTCCCCC ACTGCGGCTA CTCCATGGGG GCTGGCTCTG ATGCCGACAT        350

GGAGGCTGAC ACGGTGCTGT CCCCTGAGCA CCCCGTGCGT CTGTGGGGCC        400

GGAGCACACG GTCAGGGCGC AGCTCCTGCC TGTCCAGCCG GGCCAATTCC        450

AATCTCACAC TCACCGACAC CGAGCATGAA AACACTGAGA CTGATCATCC        500

GGGCGGCCTG CAGAACCACG CGCGGCTCCG GACGCCGCCG CCGCCGCTCT        550
```

-continued

| | |
|---|---:|
| CGCACGCCCA CACCCCCAAC CAGCACCACG CGGCCTCCAT TAACTCCCTG | 600 |
| AACCGGGGCA ACTTCACGCC GAGGAGCAAC CCCAGCCCGG CCCCCACGGA | 650 |
| CCACTCGCTC TCCGGAGAGC CCCCTGCCGG CGGCGCCCAG GAGCCTGCCC | 700 |
| ACGCCCAGGA GAACTGGCTG CTCAACAGCA ACATCCCCCT GGAGACCAGA | 750 |
| AACCTAGGCA AGCAGCCATT CCTAGGGACA TTGCAGGACA ACCTCATTGA | 800 |
| GATGGACATT CTCGGCGCCT CCCGCCATGA TGGGGCTTAC AGTGACGGGC | 850 |
| ACTTCCTCTT CAAGCCTGGA GGCACCTCCC CGCTCTTCTG CACCACATCA | 900 |
| CCAGGGTACC CACTGACGTC CAGCACAGTG TACTCTCCTC CGCCCCGACC | 950 |
| CCTGCCCCGC AGCACCTTCG CCCGGCCGGC CTTTAACCTC AAGAAGCCCT | 1000 |
| CCAAGTACTG TAACTGGAAG TGCGCAGCCC TGAGCGCCAT CGTCATCTCA | 1050 |
| GCCACTCTGG TCATCCTGCT GGCATACTTT GTGGCCATGC ACCTGTTTGG | 1100 |
| CCTAAACTGG CACCTGCAGC CGATGGAGGG GCAGATGTAT GAGATCACGG | 1150 |
| AGGACACAGC CAGCAGTTGG CCTGTGCCAA CCGACGTCTC CCTATACCCC | 1200 |
| TCAGGGGGCA CTGGCTTAGA GACCCCTGAC AGGAAAGGCA AAGGAACCAC | 1250 |
| AGAAGGAAAG CCCAGTAGTT TCTTTCCAGA GGACAGTTTC ATAGATTCTG | 1300 |
| GAGAAATTGA TGTGGGAAGG CGAGCTTCCC AGAAGATTCC TCCTGGCACT | 1350 |
| TTCTGGAGAT CTCAAGTGTT CATAGACCAT CCTGTGCATC TGAAATTCAA | 1400 |
| TGTGTCTCTG GGAAAGGCAG CCCTGGTTGG CATTTATGGC AGAAAAGGCC | 1450 |
| TCCCTCCTTC ACATACACAG TTTGACTTTG TGGAGCTGCT GGATGGCAGG | 1500 |
| AGGCTCCTAA CCCAGGAGGC GCGGAGCCTA GAGGGACCC CGCGCCAGTC | 1550 |
| TCGGGGAACT GTGCCCCCCT CCAGCCATGA GACAGGCTTC ATCCAGTATT | 1600 |
| TGGATTCAGG AATCTGGCAC TTGGCTTTTT ACAATGACGG AAAGGAGTCA | 1650 |
| GAAGTGGTTT CCTTTCTCAC CACTGCCATT | 1680 |

(2) INFORMATION FOR SEQ ID NO: 4:

(i) SEQUENCE CHARACTERISTICS:
        (A) LENGTH: 560 amino acids
        (B) TYPE: Amino Acid
        (D) TOPOLOGY: Linear (xi) SEQUENCE DESCRIPTION: SEQ ID NO: 4:

```
Met Asp Val Lys Glu Arg Lys Pro Tyr Arg Ser Leu Thr Arg Arg
 1               5                  10                  15

Arg Asp Ala Glu Arg Arg Tyr Thr Ser Ser Ser Ala Asp Ser Glu
                20                  25                  30

Glu Gly Lys Ala Pro Gln Lys Ser Tyr Ser Ser Glu Thr Leu
                35                  40                  45

Lys Ala Tyr Asp Gln Asp Ala Arg Leu Ala Tyr Gly Ser Arg Val
                50                  55                  60

Lys Asp Ile Val Pro Gln Glu Ala Glu Phe Cys Arg Thr Gly
                65                  70                  75

Ala Asn Phe Thr Leu Arg Glu Leu Gly Leu Glu Glu Val Thr Pro
                80                  85                  90

Pro His Gly Thr Leu Tyr Arg Thr Asp Ile Gly Leu Pro His Cys
                95                 100                 105

Gly Tyr Ser Met Gly Ala Gly Ser Asp Ala Asp Met Glu Ala Asp
               110                 115                 120
```

```
Thr Val Leu Ser Pro Glu His Pro Val Arg Leu Trp Gly Arg Ser
            125                 130                 135

Thr Arg Ser Gly Arg Ser Ser Cys Leu Ser Ser Arg Ala Asn Ser
            140                 145                 150

Asn Leu Thr Leu Thr Asp Thr Glu His Glu Asn Thr Glu Thr Asp
            155                 160                 165

His Pro Gly Gly Leu Gln Asn His Ala Arg Leu Arg Thr Pro Pro
            170                 175                 180

Pro Pro Leu Ser His Ala His Thr Pro Asn Gln His His Ala Ala
            185                 190                 195

Ser Ile Asn Ser Leu Asn Arg Gly Asn Phe Thr Pro Arg Ser Asn
            200                 205                 210

Pro Ser Pro Ala Pro Thr Asp His Ser Leu Ser Gly Glu Pro Pro
            215                 220                 225

Ala Gly Gly Ala Gln Glu Pro Ala His Ala Gln Glu Asn Trp Leu
            230                 235                 240

Leu Asn Ser Asn Ile Pro Leu Glu Thr Arg Asn Leu Gly Lys Gln
            245                 250                 255

Pro Phe Leu Gly Thr Leu Gln Asp Asn Leu Ile Glu Met Asp Ile
            260                 265                 270

Leu Gly Ala Ser Arg His Asp Gly Ala Tyr Ser Asp Gly His Phe
            275                 280                 285

Leu Phe Lys Pro Gly Gly Thr Ser Pro Leu Phe Cys Thr Thr Ser
            290                 295                 300

Pro Gly Tyr Pro Leu Thr Ser Ser Thr Val Tyr Ser Pro Pro Pro
            305                 310                 315

Arg Pro Leu Pro Arg Ser Thr Phe Ala Arg Pro Ala Phe Asn Leu
            320                 325                 330

Lys Lys Pro Ser Lys Tyr Cys Asn Trp Lys Cys Ala Ala Leu Ser
            335                 340                 345

Ala Ile Val Ile Ser Ala Thr Leu Val Ile Leu Leu Ala Tyr Phe
            350                 355                 360

Val Ala Met His Leu Phe Gly Leu Asn Trp His Leu Gln Pro Met
            365                 370                 375

Glu Gly Gln Met Tyr Glu Ile Thr Glu Asp Thr Ala Ser Ser Trp
            380                 385                 390

Pro Val Pro Thr Asp Val Ser Leu Tyr Pro Ser Gly Gly Thr Gly
            395                 400                 405

Leu Glu Thr Pro Asp Arg Lys Gly Lys Gly Thr Thr Glu Gly Lys
            410                 415                 420

Pro Ser Ser Phe Phe Pro Glu Asp Ser Phe Ile Asp Ser Gly Glu
            425                 430                 435

Ile Asp Val Gly Arg Arg Ala Ser Gln Lys Ile Pro Pro Gly Thr
            440                 445                 450

Phe Trp Arg Ser Gln Val Phe Ile Asp His Pro Val His Leu Lys
            455                 460                 465

Phe Asn Val Ser Leu Gly Lys Ala Ala Leu Val Gly Ile Tyr Gly
            470                 475                 480

Arg Lys Gly Leu Pro Pro Ser His Thr Gln Phe Asp Phe Val Glu
            485                 490                 495

Leu Leu Asp Gly Arg Arg Leu Leu Thr Gln Glu Ala Arg Ser Leu
            500                 505                 510
```

```
Glu Gly Thr Pro Arg Gln Ser Arg Gly Thr Val Pro Pro Ser Ser
            515                 520                 525

His Glu Thr Gly Phe Ile Gln Tyr Leu Asp Ser Gly Ile Trp His
            530                 535                 540

Leu Ala Phe Tyr Asn Asp Gly Lys Glu Ser Glu Val Val Ser Phe
            545                 550                 555

Leu Thr Thr Ala Ile
            560

(2) INFORMATION FOR SEQ ID NO: 5:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 5:

Pro Lys Asn Ser Ser Met Ile Ser Asn Thr Pro
 1               5                10  11

(2) INFORMATION FOR SEQ ID NO: 6:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 6:

His Gln Ser Leu Gly Thr Gln
 1               5       7

(2) INFORMATION FOR SEQ ID NO: 7:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 7:

His Gln Asn Leu Ser Asp Gly Lys
 1               5            8

(2) INFORMATION FOR SEQ ID NO: 8:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 8:

His Gln Asn Ile Ser Asp Gly Lys
 1               5            8

(2) INFORMATION FOR SEQ ID NO: 9:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 9:

Val Ile Ser Ser His Leu Gly Gln
 1               5            8

(2) INFORMATION FOR SEQ ID NO: 10:
```

(i) SEQUENCE CHARACTERISTICS:
    (A) LENGTH: 501 amino acids
    (B) TYPE: Amino Acid
    (D) TOPOLOGY: Linear (xi) SEQUENCE DESCRIPTION: SEQ ID NO: 10:

```
Met Asp Ile Leu Gly Ala Ser Arg His Asp Gly Ala Tyr Ser Asp
  1               5                  10                  15

Gly His Phe Leu Phe Lys Pro Gly Gly Thr Ser Pro Leu Phe Cys
                 20                  25                  30

Thr Thr Ser Pro Gly Tyr Pro Leu Thr Ser Ser Thr Val Tyr Ser
                 35                  40                  45

Pro Pro Pro Arg Pro Leu Pro Arg Ser Thr Phe Ala Arg Pro Ala
                 50                  55                  60

Phe Asn Leu Lys Lys Pro Ser Lys Tyr Cys Asn Trp Lys Cys Ala
                 65                  70                  75

Ala Leu Ser Ala Ile Val Ile Ser Ala Thr Leu Val Ile Leu Leu
                 80                  85                  90

Ala Tyr Phe Val Ala Met His Leu Phe Gly Leu Asn Trp His Leu
                 95                 100                 105

Gln Pro Met Glu Gly Gln Met Tyr Glu Ile Thr Glu Asp Thr Ala
                110                 115                 120

Ser Ser Trp Pro Val Pro Thr Asp Val Ser Leu Tyr Pro Ser Gly
                125                 130                 135

Gly Thr Gly Leu Glu Thr Pro Asp Arg Lys Gly Lys Gly Thr Thr
                140                 145                 150

Glu Gly Lys Pro Ser Ser Phe Phe Pro Glu Asp Ser Phe Ile Asp
                155                 160                 165

Ser Gly Glu Ile Asp Val Gly Arg Arg Ala Ser Gln Lys Ile Pro
                170                 175                 180

Pro Gly Thr Phe Trp Arg Ser Gln Val Phe Ile Asp His Pro Val
                185                 190                 195

His Leu Lys Phe Asn Val Ser Leu Gly Lys Ala Ala Leu Val Gly
                200                 205                 210

Ile Tyr Gly Arg Lys Gly Leu Pro Pro Ser His Thr Gln Phe Asp
                215                 220                 225

Phe Val Glu Leu Leu Asp Gly Arg Arg Leu Leu Thr Gln Glu Ala
                230                 235                 240

Arg Ser Leu Glu Gly Thr Pro Arg Gln Ser Arg Gly Thr Val Pro
                245                 250                 255

Pro Ser Ser His Glu Thr Gly Phe Ile Gln Tyr Leu Asp Ser Gly
                260                 265                 270

Ile Trp His Leu Ala Phe Tyr Asn Asp Gly Lys Glu Ser Glu Val
                275                 280                 285

Val Ser Phe Leu Thr Thr Ala Ile Ala Leu Pro Pro Arg Leu Lys
                290                 295                 300

Glu Met Lys Ser Gln Glu Ser Ala Ala Gly Ser Lys Leu Val Leu
                305                 310                 315

Arg Cys Glu Thr Ser Ser Glu Tyr Ser Ser Leu Arg Phe Lys Trp
                320                 325                 330

Phe Lys Asn Gly Asn Glu Leu Asn Arg Lys Asn Lys Pro Gln Asn
                335                 340                 345

Ile Lys Ile Gln Lys Lys Pro Gly Lys Ser Glu Leu Arg Ile Asn
                350                 355                 360
```

```
Lys Ala Ser Leu Ala Asp Ser Gly Glu Tyr Met Cys Lys Val Ile
                365                 370                 375

Ser Lys Leu Gly Asn Asp Ser Ala Ser Ala Asn Ile Thr Ile Val
                380                 385                 390

Glu Ser Asn Glu Ile Ile Thr Gly Met Pro Ala Ser Thr Glu Gly
                395                 400                 405

Ala Tyr Val Ser Ser Glu Ser Pro Ile Arg Ile Ser Val Ser Thr
                410                 415                 420

Glu Gly Ala Asn Thr Ser Ser Thr Ser Thr Ser Thr Thr Thr Gly
                425                 430                 435

Thr Ser His Leu Val Lys Cys Ala Glu Lys Glu Lys Thr Phe Cys
                440                 445                 450

Val Asn Gly Gly Glu Cys Phe Met Val Lys Asp Leu Ser Asn Pro
                455                 460                 465

Ser Arg Tyr Leu Cys Lys Cys Pro Asn Glu Phe Thr Gly Asp Arg
                470                 475                 480

Cys Gln Asn Tyr Val Met Ala Ser Phe Tyr Ser Thr Ser Thr Pro
                485                 490                 495

Phe Leu Ser Leu Pro Glu
                500 501
```

(2) INFORMATION FOR SEQ ID NO: 11:

(i) SEQUENCE CHARACTERISTICS:
        (A) LENGTH: 2387 base pairs
        (B) TYPE: Nucleic Acid
        (C) STRANDEDNESS: Single
        (D) TOPOLOGY: Linear (xi) SEQUENCE DESCRIPTION: SEQ ID NO: 11:

```
CATCCGGGCG GCCTGCAGAA CCACGCGCGG CTCCGGACGC CGCCGCCGCC         50

GCTCTCGCAC GCCCACACCC CCAACCAGCA CCACGCGGCC TCCATTAACT        100

CCCTGAACCG GGGCAACTTC ACGCCGAGGA GCAACCCCAG CCCGGCCCCC        150

ACGGACCACT CGCTCTCCGG AGAGCCCCCT GCCGGCGGCG CCCAGGAGCC        200

TGCCCACGCC CAGGAGAACT GGCTGCTCAA CAGCAACATC CCCCTGGAGA        250

CCAGAAACCT AGGCAAGCAG CCATTCCTAG GGACATTGCA GGACAACCTC        300

ATTGAGATGG ACATTCTCGG CGCCTCCCGC CATGATGGGG CTTACAGTGA        350

CGGGCACTTC CTCTTCAAGC CTGGAGGCAC CTCCCCGCTC TTCTGCACCA        400

CATCACCAGG GTACCCACTG ACGTCCAGCA CAGTGTACTC TCCTCCGCCC        450

CGACCCCTGC CCCGCAGCAC CTTCGCCCGG CCGGCCTTTA ACCTCAAGAA        500

GCCCTCCAAG TACTGTAACT GGAAGTGCGC AGCCCTGAGC GCCATCGTCA        550

TCTCAGCCAC TCTGGTCATC CTGCTGGCAT ACTTTGTGGC CATGCACCTG        600

TTTGGCCTAA ACTGGCACCT GCAGCCGATG GAGGGGCAGA TGTATGAGAT        650

CACGGAGGAC ACAGCCAGCA GTTGGCCTGT GCCAACCGAC GTCTCCCTAT        700

ACCCCTCAGG GGGCACTGGC TTAGAGACCC CTGACAGGAA AGGCAAAGGA        750

ACCACAGAAG GAAAGCCCAG TAGTTTCTTT CCAGAGGACA GTTTCATAGA        800

TTCTGGAGAA ATTGATGTGG AAGGCGAGC TTCCCAGAAG ATTCCTCCTG         850

GCACTTTCTG GAGATCTCAA GTGTTCATAG ACCATCCTGT GCATCTGAAA        900

TTCAATGTGT CTCTGGGAAA GGCAGCCCTG GTTGGCATTT ATGGCAGAAA        950
```

```
AGGCCTCCCT CCTTCACATA CACAGTTTGA CTTTGTGGAG CTGCTGGATG        1000

GCAGGAGGCT CCTAACCCAG GAGGCGCGGA GCCTAGAGGG GACCCCGCGC        1050

CAGTCTCGGG GAACTGTGCC CCCCTCCAGC CATGAGACAG GCTTCATCCA        1100

GTATTTGGAT TCAGGAATCT GGCACTTGGC TTTTTACAAT GACGGAAAGG        1150

AGTCAGAAGT GGTTTCCTTT CTCACCACTG CCATTGATTC CAGTGGTACA        1200

GGACAGAGTG CTCACGTAAC TGTTCAAGAT TCTGTGATTT TTCAGAGAAG        1250

AGGCTTGGAA TCAGCCTTGC CTCCCCGATT GAAAGAGATG AAAAGCCAGG        1300

AATCGGCTGC AGGTTCCAAA CTAGTCCTTC GGTGTGAAAC CAGTTCTGAA        1350

TACTCCTCTC TCAGATTCAA GTGGTTCAAG AATGGGAATG AATTGAATCG        1400

AAAAAACAAA CCACAAAATA TCAAGATACA AAAAAAGCCA GGGAAGTCAG        1450

AACTTCGCAT TAACAAAGCA TCACTGGCTG ATTCTGGAGA GTATATGTGC        1500

AAAGTGATCA GCAAATTAGG AAATGACAGT GCCTCTGCCA ATATCACCAT        1550

CGTGGAATCA AACGAGATCA TCACTGGTAT GCCAGCCTCA ACTGAAGGAG        1600

CATATGTGTC TTCAGAGTCT CCCATTAGAA TATCAGTATC CACAGAAGGA        1650

GCAAATACTT CTTCATCTAC ATCTACATCC ACCACTGGGA CAAGCCATCT        1700

TGTAAAATGT GCGGAGAAGG AGAAAACTTT CTGTGTGAAT GGAGGGGAGT        1750

GCTTCATGGT GAAAGACCTT TCAAACCCCT CGAGATACTT GTGCAAGTGC        1800

CCAAATGAGT TTACTGGTGA TCGCTGCCAA AACTACGTAA TGGCCAGCTT        1850

CTACAGTACG TCCACTCCCT TTCTGTCTCT GCCTGAATAG GAGCATGCTC        1900

AGTTGGTGCT GCTTTCTTGT TGCTGCATCT CCCCTCAGAT TCCACCTAGA        1950

GCTAGATGTG TCTTACCAGA TCTAATATTG ACTGCCTCTG CCTGTCGCAT        2000

GAGAACATTA ACAAAAGCAA TTGTATTACT TCCTCTGTTC GCGACTAGTT        2050

GGCTCTGAGA TACTAATAGG TGTGTGAGGC TCCGGATGTT TCTGGAATTG        2100

ATATTGAATG ATGTGATACA AATTGATAGT CAATATCAAG CAGTGAAATA        2150

TGATAATAAA GGCATTTCAA AGTCTCACTT TTATTGATAA AATAAAAATC        2200

ATTCTACTGA ACAGTCCATC TTCTTTATAC AATGACCACA TCCTGAAAAG        2250

GGTGTTGCTA AGCTGTAACC GATATGCACT TGAAATGATG GTAAGTTAAT        2300

TTTGATTCAG AATGTGTTAT TTGTCACAAA TAAACATAAT AAAAGGAGTT        2350

CAGATGTTTT TCTTCATTAA CCAAAAAAAA AAAAAA                      2387
```

ANTIBODIES THAT BIND GAMMA-HEREGULIN

RELATED APPLICATIONS

This application is a divisional of U.S. application Ser. No. 09/514,573 filed Feb. 28, 2000 (now U.S. Pat. No. 6,500,941), which is a continuation of U.S. application Ser. No. 08/891,845 filed Jul. 10, 1997 (now U.S. Pat. No. 6,096,873 issued Aug. 1, 2000), which is a non-provisional application filed under 37 CFR 1.53(b)(1), claiming priority under 35 USC Section 119(e) to provisional U.S. Application Ser. No. 60/021,640 filed on Jul. 12, 1996 (now abandoned), which applications are incorporated herein by reference.

FIELD OF THE INVENTION

This application relates to the discovery of a novel heregulin polypeptide called gamma-heregulin (γ-HRG) secreted by human breast cancer MDA-MB-175 cells, which has a unique N-terminal domain not present in hitherto-identified heregulins.

BACKGROUND OF THE INVENTION

Transduction of signals that regulate cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular substrates. Growth factor receptor protein tyrosine kinases of the class I subfamily include the 170 kDa epidermal growth factor receptor (EGFR) encoded by the erbB1 gene. erbB1 has been causally implicated in human malignancy. In particular, increased expression of this gene has been observed in more aggressive carcinomas of the breast, bladder, lung and stomach.

The second member of the class I subfamily, p185$^{neu}$, was originally identified as the product of the transforming gene from neuroblastomas of chemically treated rats. The neu gene (also called erbB2 and HER2) encodes a 185 kDa receptor protein tyrosine kinase. Amplification and/or overexpression of the human HER2 gene correlates with a poor prognosis in breast and ovarian cancers (Slamon et al., *Science* 235:177–182 (1987); and Slamon et al., *Science* 244:707–712 (1989)). Overexpression of HER2 has been correlated with other carcinomas including carcinomas of the stomach, endometrium, salivary gland, lung, kidney, colon and bladder. Accordingly, Slamon et al. in U.S. Pat. No. 4,968,603 describe and claim various diagnostic assays for determining HER2 gene amplification or expression in tumor cells. Slamon et al. discovered that the presence of multiple gene copies of HER2 oncogene in tumor cells indicates that the disease is more likely to spread beyond the primary tumor site, and that the disease may therefore require more aggressive treatment than might otherwise be indicated by other diagnostic factors. Slamon et al. conclude that the HER2 gene amplification test, together with the determination of lymph node status, provides greatly improved prognostic utility.

A further related gene, called erbB3 or HER3, has also been described. See U.S. Pat. No. 5,183,884; Kraus et al., *Proc. Natl. Acad. Sci. USA* 86:9193–9197 (1989); EP Pat Appln No 444,961A1; and Kraus et al., *Proc. Natl. Acad. Sci. USA* 90:2900–2904(1993). Kraus et al. (1989) discovered that markedly elevated levels of erbB3 mRNA were present in certain human mammary tumor cell lines indicating that erbB3, like erbB1 and erbB2, may play a role in human malignancies. Also, Kraus et al. (1993) showed that EGF-dependent activation of the ErbB3 catalytic domain of a chimeric EGFR/ErbB3 receptor resulted in a proliferative response in transfected NIH-3T3 cells. Furthermore, these researchers demonstrated that some human mammary tumor cell lines display a significant elevation of steady-state ErbB3 tyrosine phosphorylation further indicating that this receptor may play a role in human malignancies. The role of erbB3 in cancer has been explored by others. It has been found to be overexpressed in breast (Lemoine et al., *Br. J. Cancer* 66:1116–1121 (1992)), gastrointestinal (Poller et al., *J. Pathol.* 168:275–280 (1992), Rajkumar et al., *J. Pathol.* 170:271–278 (1993), and Sanidas et al., *Int. J. Cancer* 54:935–940 (1993)), and pancreatic cancers (Lemoine et al., *J. Pathol.* 168:269–273(1992), and Friess et al., *Clinical Cancer Research* 1:1413–1420 (1995)).

The class I subfamily of growth factor receptor protein tyrosine kinases has been further extended to include the HER4/Erb4 receptor. See EP Pat Appln No 599,274; Plowman et al., *Proc. Natl. Acad. Sci. USA* 90:1746–1750 (1993); and Plowman et al., *Nature* 366:473–475 (1993). Plowman et al. found that increased HER4 expression closely correlated with certain carcinomas of epithelial origin, including breast adenocarcinomas. Diagnostic methods for detection of human neoplastic conditions (especially breast cancers) which evaluate HER4 expression are described in EP Pat Appln No. 599,274.

The quest for the activator of the HER2 oncogene has lead to the discovery of a family of heregulin polypeptides. These proteins appear to result from alternate splicing of a single gene which was mapped to the short arm of human chromosome 8 by Orr-Urtreger et al., *Proc. Natl. Acad. Sci. USA* 90:1867–1871(1993).

Holmes et al. isolated and cloned a family of polypeptide activators for the HER2 receptor which they called heregulin-α(HRG-α), heregulin-β1 (HRG-β1), heregulin-β2 (HRG-β2), heregulin-β2-like (HRG-β2-like), and heregulin-β3 (HRG-β3). See Holmes et al., *Science* 256:1205–1210 (1992); WO 92/20798; and U.S. Pat. No. 5,367,060. The 45 kDa polypeptide, HRG-α, was purified from the conditioned medium of the MDA-MB-231 human breast cancer cell line. These researchers demonstrated the ability of the purified heregulin polypeptides to activate tyrosine phosphorylation of the HER2 receptor in MCF7 breast tumor cells. Furthermore, the mitogenic activity of the heregulin polypeptides on SK-BR-3 cells (which express high levels of the HER2 receptor) was illustrated. Like other growth factors which belong to the EGF family, soluble HRG polypeptides appear to be derived from a membrane bound precursor (called pro-HRG) which is proteolytically processed to release the 45 kDa soluble form. These pro-HRGs lack a N-terminal signal peptide.

While heregulins are substantially identical in the first 213 amino acid residues, they are classified into two major types, α and β, based on two variant EGF-like domains which differ in their C-terminal portions. Nevertheless, these EGF-like domains are identical in the spacing of six cysteine residues contained therein. Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-α, and 27% identical to EGF.

The 44 kDa neu differentiation factor (NDF), which is the rat equivalent of human HRG, was first described by Peles et al., *Cell,* 69:205–216 (1992); and Wen et al., *Cell,* 69:559–572 (1992). Like the HRG polypeptides, NDF has an immunoglobulin (Ig) homology domain followed by an EGF-like domain and lacks a N-terminal signal peptide. Subsequently, Wen et al., *Mol. Cell. Biol.,* 14(3):1909–1919 (1994) carried out "exhaustive cloning" to extend the family of NDFs. This work revealed six distinct fibroblastic pro-NDFs. Adopting the nomenclature of Holmes et al., the NDFs are classified as either α or β polypeptides based on the sequences of the EGF-like domains. Isoforms 1 to 4 are characterized on the basis of the variable just a membrane stretch (between the EGF-like domain and transmembrane domain). Also, isoforms a, b and c are described which have variable length cytoplasmic domains. These researchers conclude that different NDF isoforms are generated by alternative splicing and perform distinct tissue-specific functions. See also EP 505 148; WO 93/22424; and WO 94/28133 concerning NDF.

Falls et al., *Cell,* 72:801–815 (1993) describe another member of the heregulin family which they call acetylcholine receptor inducing activity (ARIA) polypeptide. The chicken-derived ARIA polypeptide stimulates synthesis of muscle acetylcholine receptors. See also WO 94/08007. ARIA is a β-type heregulin and lacks the entire spacer region rich in glycosylation sites between the Ig-like domain and EGF-like domain of HRGα, and HRGβ1–β3.

Marchionni et al., *Nature,* 362:312–318 (1993) identified several bovine-derived proteins which they call glial growth factors (GGFs). These GGFs share the Ig-like domain and EGF-like domain with the other heregulin proteins described above, but also have an amino-terminal kringle domain. GGFs generally do not have the complete glycosylated spacer region between the Ig-like domain and EGF-like domain. Only one of the GGFs, GGFII, possessed a N-terminal signal peptide. See also WO 92/18627; WO 94/00140; WO 94/04560; WO 94/26298; and WO 95/32724 which refer to GGFs and uses thereof.

Ho et al. in *J. Biol. Chem.* 270(24):14523–14532 (1995) describe another member of the heregulin family called sensory and motor neuron-derived factor (SMDF). This protein has an EGF-like domain characteristic of all other heregulin polypeptides but a distinct N-terminal domain. The major structural difference between SMDF and the other heregulin polypeptides is the lack in SMDF of the Ig-like domain and the "glyco" spacer characteristic of all the other heregulin polypeptides. Another feature of SMDF is the presence of two stretches of hydrophobic amino acids near the N-terminus.

While the heregulin polypeptides were first identified based on their ability to activate the HER2 receptor (see Holmes et al., supra), it was discovered that certain ovarian cells expressing neu and neu-transfected fibroblasts did not bind or crosslink to NDF, nor did they respond to NDF to undergo tyrosine phosphorylation (Peles et al., *EMBO J.* 12:961–971 (1993)). This indicated another cellular component was necessary for conferring full heregulin responsiveness. Carraway et al. subsequently demonstrated that $^{125}$I-rHRGβ1$_{177-244}$ bound to NIH-3T3 fibroblasts stably transfected with bovine erbB3 but not to non-transfected parental cells. Accordingly, they conclude that ErbB3 is a receptor for HRG and mediates phosphorylation of intrinsic tyrosine residues as well as phosphorylation of ErbB2 receptor in cells which express both receptors. Carraway et al., *J. Biol. Chem.* 269(19):14303–14306 (1994). Sliwkowski et al., *J. Biol. Chem.* 269(20):14661–14665 (1994) found that cells transfected with HER3 alone show low affinities for heregulin, whereas cells transfected with both HER2 and HER3 show higher affinities.

This observation correlates with the "receptor crosstalking" described previously by Kokai et al., *Cell* 58:287–292 (1989); Stern et al., *EMBO J.* 7:995–1001 (1988); and King et al., *Oncogene* 4:13–18 (1989). These researchers found that binding of EGF to the EGFR resulted in activation of the EGFR kinase domain and cross-phosphorylation of p185$^{HER2}$. This is believed to be a result of ligand-induced receptor heterodimerization and the concomitant cross-phosphorylation of the receptors within the heterodimer (Wada et al., *Cell* 61:1339–1347 (1990)).

Plowman and his colleagues have similarly studied p185$^{HER4}$/p185$^{HER2}$ activation. They expressed p185$^{HER2}$ alone, p185$^{HER4}$ alone, or the two receptors together in human T lymphocytes and demonstrated that heregulin is capable of stimulating tyrosine phosphorylation of p185$^{HER4}$, but could only stimulate p185$^{HER2}$ phosphorylation in cells expressing both receptors. Plowman et al., *Nature* 366:473–475 (1993). Thus, heregulin is the only known example of a member of the EGF growth factor family that can interact with several receptors. Carraway and Cantley, *Cell* 78:5–8 (1994).

The biological role of heregulin has been investigated by several groups. For example, Falls et al., (discussed above) found that ARIA plays a role in myotube differentiation, namely affecting the synthesis and concentration of neurotransmitter receptors in the postsynaptic muscle cells of motor neurons. Corfas and Fischbach demonstrated that ARIA also increases the number of sodium channels in chick muscle. Corfas and Fischbach, *J. Neuroscience,* 13(5): 2118–2125 (1993). It has also been shown that GGFII is mitogenic for subconfluent quiescent human myoblasts and that differentiation of clonal human myoblasts in the continuous presence of GGFII results in greater numbers of myotubes after six days of differentiation (Sklar et al., *J. Cell Biochem.,* Abst. W462, 18D, 540 (1994)). See also WO 94/26298 published Nov. 24, 1994.

Holmes et al., supra, found that HRG exerted a mitogenic effect on mammary cell lines (such as SK-BR-3 and MCF-7). The mitogenic activity of GGFs on Schwann cells has also been reported. See, e.g., Brockes et al., *J. Biol. Chem.* 255(18):8374–8377 (1980); Lemke and Brockes, *J. Neurosci.* 4:75–83 (1984); Brockes et al., *Ann. Neurol.* 20(3) :317–322 (1986); Brockes, J., *Methods in Enzym.,* 147: 217–225 (1987) and Marchionni et al., supra. Schwann cells constitute important glial cells which provide myelin sheathing around the axons of neurons, thereby forming individual nerve fibers. Thus, it is apparent that Schwann cells play an important role in the development, function and regeneration of peripheral nerves. The implications of this from a therapeutic standpoint have been addressed by Levi et al., *J. Neuroscience* 14(3):1309–1319 (1994). Levi et al. discuss the potential for construction of a cellular prosthesis comprising human Schwann cells which could be transplanted into areas of damaged spinal cord. Methods for culturing Schwann cells ex vivo have been described. See WO 94/00140 and Li et al., *J. Neuroscience* 16(6):2012–2019 (1996).

Pinkas-Kramarski et al. found that NDF seems to be expressed in neurons and glial cells in embryonic and adult rat brain and primary cultures of rat brain cells, and suggested that it may act as a survival and maturation factor for astrocytes (Pinkas-Kramarski et al., *PNAS, USA* 91:9387–9391 (1994)). Meyer and Birchmeier, *PNAS, USA* 91:1064–1068 (1994) analyzed expression of heregulin during mouse embryogenesis and in the perinatal animal using in situ hybridization and RNase protection experiments. These authors conclude that, based on expression of this molecule, heregulin plays a role in vivo as a mesenchymal and neuronal factor. Also, their findings imply that heregulin functions in the development of epithelia. Similarly, Danilenko et al., Abstract 3101, *FASEB* 8(4–5):A535 (1994), found that the interaction of NDF and the HER2 receptor is important in directing epidermal migration and differentiation during wound repair.

SUMMARY OF THE INVENTION

The invention relates to the discovery of the novel γ-HRG polypeptide and nucleic acid. This molecule, secreted by human breast cancer MDA-MB-175 cells, leads to the formation of a constitutive active receptor complex and stimulates the growth of these cells in an autocrine manner. Accordingly, the invention provides isolated γ-HRG polypeptide. This γ-HRG polypeptide is preferably substantially homogeneous and may be selected from the group consisting of a native sequence polypeptide (such as human γ-HRG of FIG. 1) and variant γ-HRG (e.g. chimeric γ-HRG). Additionally, the γ-HRG polypeptide may be selected from the group consisting of the polypeptide that is isolated from a mammal (e.g. a human), the polypeptide that is made by recombinant means, and the polypeptide that is made by synthetic means. Accordingly, the polypeptide may be unassociated with native glycosylation or may be completely unglycosylated. In preferred embodiments, the isolated γ-HRG possesses an effector function of human γ-HRG of SEQ ID NO:2 and comprises an amino acid sequence selected from the group consisting of: (a) the amino acid sequence for mature human γ-HRG in SEQ ID NO:2; (b) the naturally occurring amino acid sequence for mature γ-HRG from an animal species other than the sequence of (a); (c) naturally occurring allelic variants or isoforms of (a) or (b); and (d) the amino acid sequence of (a), (b) or (c) which has only one or two amino acid substitutions.

The invention further provides a composition (preferably one which is sterile) comprising γ-HRG and a pharmaceutically acceptable carrier. The composition may be used in a method for activating an ErbB receptor which comprises the step of contacting a cell which expresses an ErbB receptor (which may be the same or different from the ErbB receptor to be activated) with the γ-HRG polypeptide. This method may be an in vitro one, e.g. where the cell is in cell culture or an in vivo method where the cell is present in a mammal (e.g. a human patient who could benefit from ErbB receptor activation). In another embodiment, the invention provides an in vitro or in vivo method for enhancing proliferation, differentiation or survival of a cell (especially where the cell expresses an ErbB receptor at its cell surface) comprising the step of contacting the cell with the γ-HRG polypeptide. The cell may, for example, be a glial cell or muscle cell. Furthermore, the invention provides a method for detecting an ErbB receptor which comprises the step of contacting a sample suspected of containing the ErbB receptor with the γ-HRG polypeptide (e.g. labelled γ-HRG) and detecting if binding has occurred. In this manner, an assay for determining a prognosis in patients suffering from carcinoma (e.g. breast or ovarian carcinoma) is provided.

γ-HRG has a unique N-terminal domain (NTD) which is not present in other heregulins. This NTD and fragments thereof (as well the nucleic acid encoding NTD or fragments thereof) is thought to be particularly useful for the production of γ-HRG-specific reagents, e.g. anti-NTD antibodies for detecting and purifying γ-HRG as well as nucleic acid probes. Accordingly, the invention provides an isolated polypeptide comprising a consecutive sequence of at least thirty amino acids of the γ-HRG-terminal domain (NTD) of SEQ ID NO:4 or one which comprises the amino acid sequence for mature γ-HRG-terminal domain (NTD) in SEQ ID NO:4.

The NTD-specific antibodies may be used, among other things, in a method for detecting γ-HRG which comprises the step of contacting a sample suspected of containing γ-HRG with the antibody (which is optionally labelled) and detecting if binding has occurred. The antibody may also be used in a method for purifying γ-HRG which comprises the step of passing a mixture containing γ-HRG over a solid phase to which is bound the antibody and recovering the fraction containing γ-HRG.

The nucleic acid encoding the NTD of γ-HRG may be used to determine the presence of a nucleic acid molecule encoding γ-HRG in a test sample (e.g. from a mammal suspected of having, or being predisposed to cancer), comprising contacting the test sample with the isolated nucleic acid and determining whether the isolated nucleic acid hybridizes to a nucleic acid molecule in the test sample. Nucleic acid encoding the NTD of γ-HRG may also be used in hybridization assays to identify and isolate nucleic acids sharing substantial sequence identity to γ-HRG. In further embodiments, this NTD-encoding nucleic acid can be used as a primer in a polymerase chain reaction for amplifying a nucleic acid molecule encoding γ-HRG in a test sample.

The invention also provides γ-HRG-specific antagonists for use in methods where it is desirable to block γ-HRG production and/or biological activity either in vitro an in vivo. One type of antagonist is a neutralizing antibody which binds specifically to the NTD of γ-HRG. Another type of antagonist is an antisense nucleic acid molecule, e.g. one which is complementary to the nucleic acid sequence encoding the NTD and which is able to reduce production of γ-HRG polypeptide by MDA-MB-175 cells.

In other aspects, the invention provides an isolated nucleic acid molecule encoding γ-HRG (and isolated antisense nucleic acid molecules; see above). For example, the nucleic acid molecule may be selected from the group consisting of: (a) nucleic acid comprising the nucleotide sequence of the coding region of the mature γ-HRG gene in SEQ ID NO:1; (b) nucleic acid corresponding to the sequence of (a) within the scope of degeneracy of the genetic code; and (c) nucleic acid which hybridizes to DNA complementary to DNA encoding the N-terminal domain (NTD) of human γ-HRG of SEQ ID NO:2 under moderately stringent conditions and which encodes a polypeptide possessing an effector function of human γ-HRG of SEQ ID NO:2. The isolated nucleic acid molecule optionally further comprises a promoter operably linked thereto.

In other embodiments, the invention provides a vector comprising the nucleic acid molecule (e.g. an expression vector comprising the nucleic acid molecule operably linked to control sequences recognized by a host cell transformed with the vector); a host cell comprising the nucleic acid molecule; and a method of using a nucleic acid molecule encoding γ-HRG to effect production of γ-HRG which comprises the step of culturing the host cell and recovering γ-HRG from the cell culture. The isolated nucleic acid may also be used for in vivo or ex vivo gene therapy.

As an alternative to production of the γ-HRG in a transformed host cell, the invention provides a method for producing γ-HRG comprising: (a) transforming a cell containing an endogenous γ-HRG gene with a homologous DNA comprising an amplificable gene and a flanking sequence of at least about 150 base pairs that is homologous with a DNA sequence within or in proximity to the endogenous γ-HRG gene, whereby the homologous DNA integrates into the cell genome by recombination; (b) culturing the cell under conditions that select for amplification of the amplifiable gene, whereby the γ-HRG gene is also amplified; and thereafter (c) recovering γ-HRG from the cell.

The invention further provides a method for treating a mammal comprising administering a therapeutically effective amount of γ-HRG to the mammal. For example, the mammal may be suffering from a neurological or muscular disorder. Conversely, the invention provides a method for treating a mammal comprising administering to a therapeutically effective amount of a γ-HRG antagonist to the mammal. The mammal in this latter case is one which could benefit from a reduction in γ-HRG levels/biological activity (e.g. in cancer).

These and other aspects of the invention will be apparent to those skilled in the art upon consideration of the following detailed description.

BRIEF DESCRIPTION OF THE DRAWING

FIGS. 1A–C depict the cDNA (SEQ ID NO:1) and deduced amino acid sequence (SEQ ID NO:2) of γ-HRG. The hydrophobic region is underlined. The EGF-like domain is shaded, cysteine residues in the EGF-like domain are circled. N-linked glycosylation sites are marked above the nucleic acid sequence with a (•).

FIG. 2 is a schematic comparison of different HRG isoforms. Boxes represent major structural motifs of various HRG isoforms. The structural features of γ-HRG are compared with HRGβ, SMDF and GGF. The EGF-like domain (EGF) is shown as a black box. The juxtamembrane (numbered), the transmembrane (TM) region and the cytoplasmic domain are drawn as distinct boxes. The glycosylated spacer domain (Spacer domain) separates the EGF-like domain from the Ig-like domain (Ig domain) in γ-HRG, HRGβ and SMDF. The unique N-terminal sequence of γ-HRG is striped. The N-terminal regions of HRGβ, SMDF and GGF are differently shaded. GGF possesses a kringle-like motif (kringle) and a signal peptide sequence (SP) in the N-terminal region.

FIG. 3 is a displacement curve of $^{125}$I-rHRGβ1$_{(177-244)}$ binding with unlabeled γ-HRG. ErbB3- or ErbB4-immunoadhesins were incubated with $^{125}$I-rHRGβ1$_{(177-244)}$ (0.23 nM) and various amounts of γ-HRG.

FIGS. 4A and 4B show the effect of 2C4, 4D5 and ErbB4 immunoadhesins on proliferation of MDA-MB-175 (FIG. 4A) and SK-BR-3 (FIG. 4B) cells. MDA-MB-175 and SK-BR-3 cells were seeded in 96 well plates and allowed to adhere for 2 hours. Experiment was carried out in medium containing 1% serum. Anti-ErbB2 antibodies, ErbB4-immunoadhesin (H4-IgG) or medium alone were added and the cells were incubated for 2 hours at 37° C. Subsequently rHRGβ1(1 nM) or 100 nM rHRGβ1 for neutralizing the H4-IgG effect or medium alone were added and the cells were incubated for 4 days. Monolayers were washed and stained/fixed with 0.5% crystal violet. To determine cell proliferation the absorbance was measured at 540 nm.

FIGS. 5A–B are an alignment of the γ-HRG amino acid sequence (SEQ ID NO:2) with the partial amino acid sequence (SEQ ID NO:10) of the γ-HRG isoform (clone 20) identified in the Example.

FIGS. 6A–G show an alignment of the γ-HRG nucleic acid sequence (SEQ ID NO:1) with the partial nucleotide sequence (SEQ ID NO:11) of the γ-HRG isoform (clone 20) identified in the Example.

DETAILED DESCRIPTION OF THE PREFERRED EMBODIMENTS

I. Definitions

In general, the following words or phrases have the indicated definition when used in the description, examples, and claims.

Unless indicated otherwise, the term "ErbB" when used herein refers to any one or more of the mammalian ErbB receptors (i.e. ErbB1 or epidermal growth factor (EGF) receptor; ErbB2 or HER2 receptor; ErbB3 or HER3 receptor; ErbB4 or HER4 receptor; and any other member(s) of this class I tyrosine kinase family to be identified in the future) and "erbB" refers to the mammalian erbB genes encoding these receptors.

"γ-HRG" (or "gamma-heregulin") is defined herein to be any polypeptide sequence that possesses at least one biological property (as defined below) of native sequence γ-HRG of SEQ ID NO: 2. This definition encompasses not only the polypeptide isolated from a native γ-HRG source such as human MDA-MB-175 cells or from another source, such as another animal species, but also the polypeptide prepared by recombinant or synthetic methods. It also includes variant forms including functional derivatives, allelic variants, naturally occurring isoforms and analogues thereof. Sometimes the γ-HRG is "native γ-HRG" which refers to endogenous γ-HRG polypeptide which has been isolated from a mammal. The γ-HRG can also be "native sequence γ-HRG" insofar as it has the same amino acid sequence as a native γ-HRG (e.g. human γ-HRG shown in FIG. 1). However, "native sequence γ-HRG" encompasses the polypeptide produced by recombinant or synthetic means. "Mature γ-HRG" is soluble or secreted γ-HRG released from the cell (i.e. lacking amino-terminal sequence). γ-HRG "isoforms" are naturally occurring polypeptides which comprise at least part of the N-terminal domain (see below) of γ-HRG. An example of a γ-HRG isoform is described in the Example below.

Optionally, the γ-HRG is not associated with native glycosylation. "Native glycosylation" refers to the carbohydrate moieties which are covalently attached to native γ-HRG when it is produced in the mammalian cell from which the native γ-HRG is derived. Accordingly, human γ-HRG produced in a non-human cell could be described as not being associated with native glycosylation, for example. Sometimes, the γ-HRG is not associated with any glycosylation whatsoever (e.g. as a result of being produced recombinantly in a prokaryote).

γ-HRG has a unique amino terminal domain which distinguishes this protein from previously described heregulin polypeptides. This is designated the "N-terminal domain" or "NTD" herein (i.e. from about residue 1 to about residue 560 of FIG. 1 (SEQ ID NO:4 encoded by the nucleic acid sequence of SEQ ID NO:3)). "Mature" NTD is NTD released from the cell surface. However, the expression "NTD" includes functional equivalents of the NTD depicted in FIG. 1.

The term "γ-HRG variant" encompasses γ-HRG polypeptides wherein one or more amino acid residues are added at the — or C-terminus of, or within, the γ-HRG sequence of FIG. 1; one or more amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active γ-HRG variant will be "substantially homologous" to the amino acid sequence of FIG. 1 and therefore will generally have an amino acid sequence having at least about 70% amino acid sequence identity with human γ-HRG shown in FIG. 1, preferably at least about 75%, more preferably at least about 80%, still more preferably at least about 85%, even more preferably at least about 90%, and most preferably at least about 95%.

One type of γ-HRG variant is a "γ-HRG fragment", which is a portion of a naturally occurring full-length γ-HRG sequence having one or more amino acid residues or carbohydrate units deleted. The deleted amino acid residue(s) may occur anywhere in the polypeptide, including at either the N-terminal or C-terminal end or internally. The fragment will usually share at least one biological property in common with γ-HRG. γ-HRG fragments will have a consecutive sequence of at least 20, 30, 40, 50, or 100 amino acid residues of the NTD of γ-HRG. The preferred fragments have about 30–150 residues which are identical to the sequence of human γ-HRG in SEQ ID NO:2.

Another type of γ-HRG variant is "chimeric γ-HRG", which term encompasses a polypeptide comprising full-length γ-HRG or a fragment thereof fused or bonded to a heterologous polypeptide. The chimera will normally share at least one biological property in common with γ-HRG. Examples of chimeric γ-HRGs include immunoadhesins and epitope tagged γ-HRG. In another embodiment, the heterologous polypeptide is thioredoxin, a salvage receptor binding epitope, cytotoxic polypeptide or enzyme (e.g., one which converts a prodrug to an active drug).

The term "immunoadhesin" is used interchangeably with the expression "γ-HRG-immunoglobulin chimera" and refers to a chimeric molecule that combines a biologically active portion of the γ-HRG with an immunoglobulin sequence. The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$ or $IgG_3$.

The term "epitope tagged" when used herein refers to a chimeric polypeptide comprising the entire γ-HRG, or a fragment thereof, fused to a "tag polypeptide". The tag polypeptide has enough residues to provide an epitope against which an antibody thereagainst can be made, yet is short enough such that it does not interfere with activity of the γ-HRG. The tag polypeptide preferably is fairly unique so that the antibody thereagainst does not substantially cross-react with other epitopes. Suitable tag polypeptides generally have at least 6 amino acid residues and usually between about 8–50 amino acid residues (preferably between about 9–30 residues).

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof. Also, the term includes oncogene product/tyrosine kinase inhibitors, such as the bicyclic ansamycins disclosed in WO 94/22867; 1,2-bis(arylamino) benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example).

A "chemotherapeutic agent" is a chemical compound useful in the treatment of cancer. Examples of chemotherapeutic agents include Adriamycin, Doxorubicin,5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Carminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

The term "prodrug" as used in this application refers to a precursor or derivative form of a pharmaceutically active substance that is less cytotoxic to tumor cells compared to the parent drug and is capable of being enzymatically activated or converted into the more active parent form. The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

"Isolated γ-HRG", "highly purified γ-HRG" and "substantially homogeneous γ-HRG" are used interchangeably and mean γ-HRG that has been purified from a γ-HRG source or has been prepared by recombinant or synthetic methods and is sufficiently free of other peptides or proteins (a) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (b) to homogeneity by SDS-PAGE under non-reducing or reducing conditions using Coomassie blue or, preferably, silver stain. Homogeneity here means less than about 5% contamination with other source proteins.

"Biological property" when used in conjunction with "γ-HRG" means having an effector or antigenic function or activity that is directly or indirectly caused or performed by native sequence γ-HRG of SEQ ID NO: 2 (whether in its native or denatured conformation).

"Effector functions" include receptor activation (e.g. activation of the ErbB2, ErbB3 and/or ErbB4 receptor); enhancement of survival, differentiation and/or proliferation of cells having one or more of these receptors (e.g. SK-BR-3 cells, Schwann cells, hepatocytes, glioblastoma cells, epithelial cells, muscle cells, astrocytes and/or oligodendrocytes); receptor binding (e.g. to the ErbB2, ErbB3 and/or ErbB4 receptor); mitogenic activity; inducing formation of ion channels (e.g. $Na^+$ channel) in a cell membrane; inducing acetylcholine receptor synthesis at the neuromuscular junction; enhancing formation of a synaptic junction between a neuron and a muscle, nerve or glandular cell; downregulation of estrogen receptor; and cell internalization (possibly associated with nuclear localization). Principle effector functions of native sequence γ-HRG are those demonstrated in the example below, i.e., an ability to bind to the ErbB3 and/or ErbB4 receptor; an ability to activate an ErbB receptor, e.g. the ErbB2/ErbB3 and/or ErbB2/ErbB4 receptor complexes (as determined in the tyrosine phosphorylation assay); and/or the ability to induce cell proliferation.

An "antigenic function" means possession of an epitope or antigenic site that is capable of cross-reacting with antibodies raised against the unique N-terminal domain (NTD) of native sequence γ-HRG, wherein such antibodies do not significantly cross-react with other known heregulin polypeptides. The principal antigenic function of a γ-HRG polypeptide is that it binds with an affinity of at least about $10^6$ L/mole to an antibody which binds specifically to the NTD of γ-HRG. Ordinarily, the polypeptide binds with an affinity of at least about $10^7$ L/mole.

"Biologically active" when used in conjunction with "γ-HRG" means a γ-HRG polypeptide that exhibits or shares an effector function of native sequence γ-HRG and that may (but need not) in addition possess an antigenic function.

"Antigenically active" γ-HRG is defined as a polypeptide that possesses an antigenic function of γ-HRG and that may (but need not) in addition possess an effector function.

"Percent amino acid sequence identity" with respect to the γ-HRG sequence is defined herein as the percentage of amino acid residues in the candidate sequence that are identical with the residues in the γ-HRG sequence having the deduced amino acid sequence described in FIG. 1, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the γ-HRG sequence shall be construed as affecting sequence identity or homology.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

"Determining disease status" refers to the act of determining likelihood of patient survival and time to relapse for neoplastic diseases, particularly breast, ovarian, stomach, endometrial, salivary gland, lung, kidney, colon, and bladder carcinomas. In particular, γ-HRG can be used to quantify erbB (e.g., erbB2, erbB3 or erbB4, but normally erbB2) overexpression in cancerous tissue taken from a patient suffering from carcinoma. This can also be referred to as "determining the proper course of treatment for patients suffering from cancer". For example, those patients characterized by erbB2 overexpression may require more aggressive treatment (e.g. chemo- or radiotherapy treatment) than might otherwise be indicated by other diagnostic factors. This phrase encompasses diagnosing patients suffering from high grade ductal carcinoma in situ. See, e.g., Disis et al., *Cancer Research*, 54:16–20 (1994).

The word "sample" refers to tissue, body fluid, or a cell from a patient. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues will be obtained and appropriately prepared. Other patient samples, including urine, tear drops, serum, cerebrospinal fluid, feces, sputum, cell extracts etc will also be useful for particular tumors.

The expression "labelled" when used herein refers to a molecule (e.g γ-HRG or anti-γ-HRG antibody) which has been conjugated, directly or indirectly, with a detectable compound or composition. The label may be detectable by itself (e.g. radioisotope labels or fluorescent labels) or, in the case of an enzymatic label, may catalyze a chemical alteration of a substrate compound or composition which is detectable.

By "solid phase" is meant a non-aqueous matrix to which a reagent of interest (e.g., γ-HRG or an antibody thereto) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

The phrase "activating an ErbB receptor" refers to the act of causing the intracellular kinase domain of an ErbB receptor to phosphorylate tyrosine residues. Generally, this will involve binding of γ-HRG to an receptor complex of two or more ErbB receptors (e.g., an ErbB2/ErbB3 or ErbB2/ErbB4 complex) which activates a kinase domain of one or more of those receptors and thereby results in phosphorylation of tyrosine residues in one or more of the receptors, and/or phosphorylation of tyrosine residues in additional substrate polypeptides(s). ErbB receptor phosphorylation can be quantified using the tyrosine phosphorylation assays described below.

The expression "enhancing survival of a cell" refers to the act of increasing the period of existence of a cell, relative to an untreated cell which has not been exposed to γ-HRG, either in vitro or in vivo.

The phrase "enhancing proliferation of a cell" encompasses the step of increasing the extent of growth and/or reproduction of the cell, relative to an untreated cell, either in vitro or in vivo. An increase in cell proliferation in cell culture can be detected by counting the number of cells before and after exposure to γ-HRG (see the Example below). The extent of proliferation can be quantified via microscopic examination of the degree of confluency. Cell proliferation can also be quantified by measuring $^3$H uptake by the cells.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g. identifying morphological changes in the cell).

A "glial cell" is derived from the central and peripheral nervous system and can be selected from oligodendroglial, astrocyte, ependymal, or microglial cells as well as satellite cells of ganglia and the neurolemmal or Schwann cells around peripheral nerve fibers.

"Muscle cells" include skeletal, cardiac or smooth muscle tissue cells. This term encompasses those cells which differentiate to form more specialized muscle cells (e.g. myoblasts).

"Isolated γ-HRG nucleic acid" is RNA or DNA free from at least one contaminating source nucleic acid with which it is normally associated in the natural source and preferably substantially free of any other mammalian RNA or DNA. The phrase "free from at least one contaminating source nucleic acid with which it is normally associated" includes the case where the nucleic acid is present in the source or natural cell but is in a different chromosomal location or is otherwise flanked by nucleic acid sequences not normally found in the source cell. An example of isolated γ-HRG nucleic acid is RNA or DNA that encodes a biologically active γ-HRG sharing at least 75%, more preferably at least 80%, still more preferably at least 85%, even more preferably 90%, and most preferably 95% sequence identity with the human γ-HRG shown in FIG. 1.

"Stringent conditions" are those that (a) employ low ionic strength and high temperature for washing, for example, 0.015 M NaCl/0.0015 M sodium citrate/0.1% NaDodSO$_4$ (SDS) at 50° C., or (b) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/mL), 0.1% SDS, and 10% dextran sulfate at 42° C., with washes at 42° C. in 0.2×SSC and 0.1% SDS.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and % SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc., as necessary to accommodate factors such as probe length and the like.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A γ-HRG "antagonist" is a molecule which prevents, or interferes with, a γ-HRG effector function (e.g. a molecule which prevents or interferes with binding and/or activation of an ErbB receptor by γ-HRG). Such molecules can be screened for their ability to competitively inhibit ErbB receptor activation by γ-HRG in the tyrosine phosphorylation assay disclosed herein, for example. Preferred antagonists are those which do not substantially interfere with the interaction of other heregulin polypeptides with ErbB receptor(s). Examples of γ-HRG antagonists include neutralizing antibodies against γ-HRG and antisense polynucleotides against the γ-HRG gene.

The terms "antisense oligodeoxynucleotide" and "antisense oligo" refer to a polynucleotide which hybridizes with an area of γ-HRG mRNA or DNA and thereby prevents or reduces production of γ-HRG polypeptide in vitro or in vivo. Preferred antisense polynucleotides are those which are complementary to at least a portion of the γ-HRG NTD-coding region of FIG. 1. This term encompasses "modified" polynucleotides, examples of which are described herein.

The term "antibody" is used in the broadest sense and specifically covers single anti-γ-HRG monoclonal antibodies and anti-γ-HRG antibody compositions with polyepitopic specificity (including neutralizing and non-neutralizing antibodies). The antibody of particular interest herein is one which does not significantly cross-react with other known heregulin proteins, such as those described in the background section above and thus is one which "binds specifically" to γ-HRG. Hence, antibodies which bind to the unique NTD of γ-HRG may be particularly useful. In such embodiments, the extent of binding of the antibody to non-γ-HRG proteins will be less than 10% as determined by radioimmunoprecipitation (RIA), for example.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-γ-HRG antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab)$_2$, and Fv), so long as they exhibit the desired biological activity. (See e.g., U.S. Pat. No. 4,816,567 and Mage & Lamoyi, in *Monoclonal Antibody Production Techniques and Applications*, pp.79–97 (Marcel Dekker, Inc.), New York (1987)).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods (U.S. Pat. No. 4,816,567). The "monoclonal antibodies" may also be isolated from phage libraries generated using the techniques described in McCafferty et al., *Nature* 348:552–554 (1990), for example.

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

By "neutralizing antibody" is meant an antibody molecule as herein defined which is able to block or significantly reduce an effector function of native sequence γ-HRG. For example, a neutralizing antibody may inhibit or reduce the ability of γ-HRG to activate an ErbB receptor in the tyrosine phosphorylation assay described herein. The neutralizing antibody may also block the mitogenic activity of γ-HRG in the cell proliferation assay disclosed herein.

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as sheep, dogs, horses, cats, cows, etc. Preferably, the mammal herein is human.

"Pharmaceutically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, polyethylene glycol (PEG), and Pluronics™.

A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes.

II. Modes for Practicing the Invention

1. γ-HRG Polypeptide & Nucleic Acid

The DNA and amino acid sequences of human γ-HRG are depicted in FIG. 1. It is contemplated that the novel γ-HRG described herein may be a member of a family of growth factors having suitable sequence identity that their DNA may hybridize to the DNA in the unique N-terminal domain (NTD) of FIG. 1 (or fragments thereof) under moderately stringent to stringent conditions. An example of such γ-HRG variant is the isoform shown in FIG. 5. Thus, a further aspect of this invention includes DNA which hybridizes under moderately stringent to stringent conditions with the DNA encoding the NTD of γ-HRG. Techniques for isolating such native sequence γ-HRG molecules and making variant γ-HRG follow.

Techniques suitable for the production of γ-HRG are well known in the art and include isolating γ-HRG from an endogenous source of the polypeptide, peptide synthesis (using a peptide synthesizer) and recombinant techniques (or any combination of these techniques). The preferred technique for production of γ-HRG is a recombinant technique to be described below. See also U.S. Pat. No. 5,364,934 with respect to vectors, host cells, etc for the recombinant production of γ-HRG.

To produce γ-HRG polypeptide, the DNA encoding γ-HRG is isolated (e.g. from a cDNA library as disclosed in Example 1 below) and operably linked to other nucleic acid in a suitable vector. The DNA thus isolated may be mutated so as to enhance expression depending on the expression system selected. For example, nucleotide substitutions may be made which avoid 5' stem and loop structures in the transcribed mRNA and/or to provide condons that are more readily transcribed by the selected host (e.g. the well-known preference codons for *E. coli* or yeast expression). The vector is a plasmid or other DNA that is capable of replicating within a host cell and can be used for cloning (i.e. to produce usable quantities of the nucleic acid) and/or to direct expression of γ-HRG. Vector design depends, among other things, on the intended use and host cell for the vector. The vector components generally include, but are not limited to, one or more of the following: an N-terminal signal sequence, an origin of replication, one or more marker genes, an enhancer element, a promoter, an operator sequence, a ribosome binding site, and a transcription termination sequence.

A particularly useful plasmid for mammalian cell culture production of γ-HRG is pRK5 (EP 307,247) and derivatives thereof, or pSVI6B (WO 91/08291 published Jun. 13, 1991). Another useful vector is disclosed in WO 96/04391. A host cell is generally transformed with the vector. Suitable host cells for cloning or expressing the vectors herein are prokaryote host cells (such as *E. col*, strains of *Bacillus, Pseudomonas* and other bacteria), yeast and other eukaryotic microbes, and higher eukaryote cells (such as Chinese hamster ovary (CHO) cells and other mammalian cells). The cells may also be present in live animals (for example, in cows, goats or sheep). Insect cells may also be used. Cloning and expression methodologies are well known in the art. To obtain expression of γ-HRG, an expression vector is introduced into host cells by transformation or transfection and the resulting recombinant host cells are cultured in conventional nutrient media, modified as appropriate for inducing promoters, selecting recombinant cells, or amplifying γ-HRG DNA. In general, principles, protocols, and practical techniques for maximizing the productivity of in vitro mammalian cell cultures can be found in *Mammalian Cell Biotechnology: a Practical Approach*, M. Butler, ed. (IRL Press, 1991).

The terms "transformation" and "transfection" are used interchangeably herein and refer to the process of introducing DNA into a cell. Following transformation or transfection, the γ-HRG DNA may integrate into the host cell genome, or may exist as an extrachromosomal element. If prokaryotic cells or cells that contain substantial cell wall constructions are used as hosts, the preferred methods of transfection of the cells with DNA is the calcium treatment method described by Cohen et al., *Proc. Natl. Acad. Sci. U.S.A.,* 69:2110–2114 (1972) or the polyethylene glycol method of Chung et al., *Nuc. Acids. Res.* 16:3580 (1988). If yeast are used as the host, transfection is generally accomplished using polyethylene glycol, as taught by Hinnen, *Proc. Natl. Acad. Sci. U.S.A.,* 75:1929–1933 (1978). If mammalian cells are used as host cells, transfection generally is carried out by the calcium phosphate precipitation method, Graham et al., *Virology* 52:546 (1978), Gorman et al., *DNA and Protein Eng. Tech.* 2:3–10 (1990). However, other known methods for introducing DNA into prokaryotic and eukaryotic cells, such as nuclear injection, electroporation, or protoplast fusion also are suitable for use in this invention.

Particularly useful in this invention are expression vectors that provide for the transient expression in mammalian cells of DNA encoding γ-HRG. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties.

It is further envisioned that the γ-HRG of this invention may be produced by homologous recombination, as provided for in WO 91/06667, published May 16, 1991. Briefly, this method involves transforming a cell containing an endogenous γ-HRG gene with a homologous DNA, which homologous DNA comprises (a) an amplifiable gene (e.g. a gene encoding dihydrofolate reductase (DHFR)), and (b) at least one flanking sequence, having a length of at least about 150 base pairs, which is homologous with a nucleotide sequence in the cell genome that is within or in proximity to the gene encoding γ-HRG. The transformation is carried out under conditions such that the homologous DNA integrates into the cell genome by recombination. Cells having integrated the homologous DNA are then subjected to conditions which select for amplification of the amplifiable gene, whereby the γ-HRG gene is amplified concomitantly. The resulting cells are then screened for production of desired amounts of γ-HRG. Flanking sequences that are in proximity to a gene encoding γ-HRG are readily identified, for example, by the method of genomic walking, using as a starting point the nucleotide sequence of γ-HRG of FIG. 1.

γ-HRG preferably is recovered from the culture medium as a secreted polypeptide, although it also may be recovered from host cell lysates. As a first step, the particulate debris, either host cells or lysed fragments, is removed, for example, by centrifugation or ultrafiltration; optionally, the protein may be concentrated with a commercially available protein concentration filter, followed by separating the γ-HRG from other impurities by one or more purification procedures selected from: fractionation on an immunoaffinity column; fractionation on an ion-exchange column; ammonium sulphate or ethanol precipitation; reverse phase HPLC; chromatography on silica; chromatography on heparin Sepharose; chromatography on a cation exchange resin; chromatofocusing; SDS-PAGE; and gel filtration (e.g. using a High Load Superdex™ 75 prep grade column, see Example below). Where the γ-HRG is expressed initially as an insoluble, aggregated form (especially in bacterial host cells), it may be necessary to solubilize and renature the γ-HRG using techniques available in the art for solubilizing and renaturing recombinant protein refractile bodies (see e.g., U.S. Pat. No. 4,511,502).

γ-HRG variants (see below) are recovered in the same fashion as native sequence γ-HRG, taking account of any substantial changes in properties occasioned by the variation. For example, preparation of epitope tagged γ-HRG, facilitates purification using an immunoaffinity column containing antibody to the epitope to adsorb the fusion polypeptide. Immunoaffinity columns such as a rabbit polyclonal anti-γ-HRG column can be employed to absorb the γ-HRG variant by binding it to at least one remaining immune epitope.

Amino acid sequence variants of native sequence γ-HRG are prepared by introducing appropriate nucleotide changes into the native sequence γ-HRG DNA, or by in vitro synthesis of the desired γ-HRG polypeptide. Such variants include, for example, deletions from, or insertions or substitutions of, residues in the amino acid sequence shown for human γ-HRG in FIG. 1. The amino acid changes also may alter post-translational processes of the native sequence γ-HRG, such as changing the number or position of N- and/or O-linked glycosylation sites. Potential N-linked glycosylation sites are shown in FIG. 1. Generally, the Asn residue will be replaced with a Gln, but other substitutions or deletions are possible.

A useful method for identification of certain residues or regions of the native γ-HRG polypeptide that are preferred locations for mutagenesis is "alanine scanning mutagenesis" as described by Cunningham and Wells, *Science* 244:1081–1085 (1989).

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. Deletions may be introduced into regions of low homology among various mammalian γ-HRGs to modify the activity of γ-HRG. Deletions from γ-HRG in the EGF-like domain will be more likely to modify the biological activity of γ-HRG more significantly. An exemplary γ-HRG deletion mutant is γ-HRG with residues 749–768 in FIG. 1 deleted. Other exemplary deletions include native sequence γ-HRG with one or more of the N-linked glycosylation sites identified in FIG. 1 deleted and/or any one or more of the residues associated with the potential protease cleavage sites removed (i.e. any one or more of residues 411–414, 440–441, 481–482, 500–501, 606–607 removed) and/or with any one or more cysteine residues removed. Regions of interest in the γ-HRG amino acid sequence of FIG. 1 include residues 1–748 (i.e. γ-HRG lacking the β3 C-terminal domain); 1–703 (i.e. γ-HRG lacking the EGF-like domain); 1–569 (i.e. γ-HRG lacking the EGF-like domain and spacer domain); 1–560 (i.e. γ-HRG lacking the EGF-like domain, spacer domain and Ig domain); 342–363 (the hydrophobic region); 364–560; 364–768; 411–560; 411–768; 412–560; 412–768; 413–560; 413–768; 414–560; 414–768; 415–560; 415–768; 441–560; 441–768; 482–560; 482–768; 501–560; 501–768; 607–560; 607–768. These regions can be used in the production of γ-HRG polypeptides which consist essentially of, or comprise, these regions. Such deletion mutants may further comprise additional internal deletions and/or substitutions and/or may be fused to a heterologous polypeptide, e.g., an immunogenic polypeptide, for use in generating anti-γ-HRG antibodies. These mutants may also comprise an additional carboxyl or amino-terminal amino acid residue (e.g. an amino-terminal methionyl residue).

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature γ-HRG sequence) may range generally from about 1 to 10 residues, more preferably 1 to 5, most preferably 1 to 3. Insertions are preferably made in even numbers of residues, but this is not required. Examples of terminal insertions include γ-HRG with an N-terminal methionyl residue, an artifact of the direct production of γ-HRG in recombinant cell culture.

A preferred type of insertion variant is chimeric γ-HRG. Fusion proteins comprising γ-HRG linked to a heterologous polypeptide can be constructed using recombinant DNA techniques, or the heterologous polypeptide can be covalently bound to the γ-HRG polypeptide by techniques well known in the art such as the use of the heterobifunctional crosslinking reagents. Exemplary coupling agents include N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Chimeric γ-HRG polypeptides include fusions of γ-HRG with immunogenic polypeptides, e.g., bacterial polypeptides such as β-lactamase or an enzyme encoded by the *E. coli* trp locus, or yeast protein, and fusions with proteins such as albumin, or ferritin, as described in WO 89/02922 published Apr. 6, 1989. Another example of chimeric γ-HRG is the thioredoxin fusion protein described in the Example herein.

In one embodiment, the chimeric polypeptide comprises a fusion of the γ-HRG (or a fragment thereof) with a tag polypeptide which provides an epitope to which an anti-tag antibody can selectively bind. The epitope tag is generally proved at the amino- or carboxyl-terminus of the γ-HRG. Such epitope tagged forms of the γ-HRG are desirable, as the presence thereof can be detected using a labelled antibody against the tag polypeptide. Also, provision of the epitope tag enables the γ-HRG to be readily purified by affinity purification using the anti-tag antibody. Tag polypeptides and their respective antibodies are well known in the art. Examples include the flu HA tag polypeptide and its antibody 12CA5, (Field et al., *Mol. Cell. Biol.* 8:2159–2165 (1988)); the c-myc tag and the 8F9, 3C7, 6E10, G4, B7 and 9E10 antibodies thereto (Evan et al., *Molecular and Cellular Biology* 5(12):3610–3616 (1985)); and the Herpes Simplex virus glycoprotein D (gD) tag and its antibody (Paborsky et al., *Protein Engineering* 3(6):547–553 (1990)).

The chimeric γ-HRG may also comprise an immunoadhesin having a longer half-life than native γ-HRG. Immunoadhesins constructed from a polypeptide linked to a heterologous immunoglobulin constant domain sequence are known in the art.

The simplest and most straightforward immunoadhesin design combines γ-HRG with the hinge and Fc regions of an immunoglobulin heavy chain. Ordinarily, when preparing the γ-HRG-immunoglobulin chimeras of the present invention, nucleic acid encoding the γ-HRG, or a fragment thereof, will be fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. Chimeric γ-HRG is most conveniently constructed by fusing the cDNA sequence encoding the γ-HRG portion in-frame to the tag polypeptide or immunoglobulin DNA sequence, for example, and expressing the resultant DNA fusion construct in appropriate host cells.

Another type of chimeric γ-HRG which is encompassed by the present invention is γ-HRG fused with a cytotoxic polypeptide (e.g. an enzymatically active toxin of bacterial, fungal, plant or animal origin, or fragments thereof). Alternatively, the toxin may be covalently attached to isolated γ-HRG. Enzymatically active toxins and fragments thereof which can be used include diphtheria A chain, nonbinding active fragments of diphtheria toxin, exotoxin A chain (from *Pseudomonas aeruginosa*), ricin A (e.g. ricin A chain), abrin A chain, modeccin A chain, alpha-sarcin *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes.

A still further type of chimeric γ-HRG, is γ-HRG polypeptide fused with a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. The enzyme component of such a chimeric molecule includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457–458 (1987)).

Yet a further type of chimeric polypeptide is γ-HRG fused to a salvage receptor binding epitope. Such chimeric molecules may have enhanced serum half-lives when compared to native sequence γ-HRG. The phrase "long half-life" as used in connection with γ-HRG derivatives, concerns γ-HRG derivatives having a longer plasma half-life and/or slower clearance than a corresponding native sequence γ-HRG.

A systematic method for preparing such a chimeric polypeptide having an increased in vivo half-life comprises several steps. The first involves identifying the sequence and conformation of a salvage receptor binding epitope of an Fc region of an IgG molecule. Once this epitope is identified, the sequence of the γ-HRG is modified to include the sequence and conformation of the identified binding epitope. After the sequence is mutated, the γ-HRG variant is tested to see if it has a longer in vivo half-life than that of the original molecule. If the γ-HRG variant does not have a longer in vivo half-life upon testing, its sequence is further altered to include the sequence and conformation of the identified binding epitope. The altered γ-HRG is tested for longer in vivo half-life, and this process is continued until a molecule is obtained that exhibits a longer in vivo half-life.

The salvage receptor binding epitope generally constitutes a region wherein any one or more amino acid residues from one or two loops of a Fc domain are transferred to the γ-HRG. Even more preferably, three or more residues from one or two loops of the Fc domain are transferred. Still more preferred, the epitope is taken from the CH2 domain of the Fc region (e.g., of an IgG).

In one most preferred embodiment, the salvage receptor binding epitope comprises the sequence (5' to 3'): PKNSSMISNTP (SEQ ID NO:5), and optionally further comprises a sequence selected from the group consisting of HQSLGTQ (SEQ ID NO:6), HQNLSDGK (SEQ ID NO:7), HQNISDGK (SEQ ID NO:8), or VISSHLGQ (SEQ ID NO:9). In another most preferred embodiment, the salvage receptor binding epitope is a polypeptide containing the sequence(s) (5' to 3'): HQNLSDGK (SEQ ID NO:7), HQNISDGK (SEQ ID NO:8), or VISSHLGQ (SEQ ID NO:9) and the sequence: PKNSSMISNTP (SEQ ID NO:5).

Alternatively, γ-HRG may be fused to a molecule (such as an antibody) which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to an erbB-expressing cell. Similarly, chimeric γ-HRG polypeptides are contemplated herein which localize cytotoxic agents to cells which express an erbB gene. For example, the heterologous polypeptide in such a chimeric γ-HRG polypeptide may be one which binds the cytotoxic agent (e.g. antibodies directed against saporin, anti-interferon-α, vinca alkaloid, ricin A chain, methotrexate or radioactive isotope hapten).

A third group of variants are amino acid substitution variants. These variants have at least one amino acid residue in the native sequence γ-HRG molecule removed and a different residue inserted in its place. For example, the substitution variant may be one which differs from the amino acid sequence shown in FIG. 1 for mature γ-HRG by the substitution of one amino acid for another at one, two, three or more positions within the FIG. 1 amino acid sequence.

Variations in the native sequence as described above can be made using any of the techniques and guidelines set forth in conservative and non-conservative mutations set forth in U.S. Pat. No. 5,364,934. See especially Table 1 therein and the discussion surrounding this table for guidance on selecting amino acids to change, add, or delete.

Any cysteine residues not involved in maintaining the proper conformation of native γ-HRG also may be substituted, generally with serine, to improve the oxidative stability of the molecule and prevent aberrant crosslinking. Also, residues in potential protease cleavage sites (i.e. any one or more of residues 411–414, 440–441, 481–482, 500–501, 606–607) may be replaced by other residues.

Representative substitutions include γ-HRG with the β-type EGF-like domain substituted with an α-type EGF-like domain, and γ-HRG with the β-type EGF-like domain replaced with the β-type EGF-like domain of rat NDF or ARIA. Further exemplary substitutions of human γ-HRG of FIG. 1 include any one or more of the following substitutions: hγ-HRG (Cys297→Ser), hγ-HRG (Cys639→Ser), hγ-HRG (Pro90→Ala), hγ-HRG (His159→Arg), hγ-HRG (Glu 237→Asp), hγ-HRG (Asn329→Gln), hγ-HRG (Leu365→Val), hγ-HRG (Val396→Leu), hγ-HRG (Gln455→Asn), hγ-HRG (Val468→Leu), hγ-HRG (Thr520→Ser), hγ-HRG (Lys 570→Arg), hγ-HRG (Leu 593→Ala), hγ-HRG (Val657→Ala), hγ-HRG (Asn467→Gln), hγ-HRG (Asn 691→Gln).

Nucleic acid molecules encoding amino acid sequence variants of native sequence γ-HRG are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of native sequence γ-HRG.

Covalent modifications of γ-HRG polypeptides are included within the scope of this invention. Both native sequence γ-HRG and amino acid sequence variants thereof may be covalently modified. Covalent modifications of γ-HRG or fragments thereof may be introduced into the molecule by reacting targeted amino acid residues of the γ-HRG or fragments thereof with an organic derivatizing agent that is capable of reacting with selected side chains or the N- or C-terminal residues. See U.S. Pat. No. 5,364,934 concerning potential covalent modifications of γ-HRG.

For tumor targeting, it may be beneficial to covalently conjugate γ-HRG with a cytotoxic agent, such as those described above. For example, a variety of radionuclides (e.g. $^{212}$Bi, $^{131}$I, $^{131}$In, $^{90}$Y and $^{186}$Re) are available for the production of radioconjugated γ-HRG. Carbon-14-labeled 1-isothiocyanatobenzyl-3-methyldiethylene triaminepentaacetic acid (MX-DTPA) is an exemplary chelating agent for conjugation of radionucleotide to the γ-HRG. See WO94/11026.

Another type of covalent modification of γ-HRG comprises linking the γ-HRG polypeptide to one of a variety of nonproteinaceous polymers, e.g., polyethylene glycol, polypropylene glycol, polyoxyalkylenes, or copolymers of polyethylene glycol and polypropylene glycol. γ-HRG also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

Once amino acid sequence variants and covalent variants have been made, it is routine to screen for those molecules which are biologically and/or antigenically active. Competitive-type immunoassays can be employed for determining whether the variant is able to cross-react with antibodies raised against native sequence γ-HRG. Other potential modifications of protein or polypeptide properties such as redox or thermal stability, hydrophobicity, susceptibility to proteolytic degradation, or the tendency to aggregate with carriers or into multimers are assayed by methods well known in the art.

Generally, the variants of interest will have any one or more of the following properties: (a) the ability to bind to ErbB3 and/or ErbB4; (b) the ability to activate ErbB receptor(s) in ErbB2/ErbB3 and/or ErbB2/ErbB4 receptor complexes; and (c) the ability to stimulate proliferation of cells which express the ErbB2 and ErbB3 receptor and/or the ErbB2 and ErbB4 receptor.

To screen for property (a), the ability of the γ-HRG variant to bind to either or both the ErbB3 and ErbB4 receptor can be readily determined in vitro. For example, immunoadhesin forms of these receptors can be generated (see below) and the ErbB3 or ErbB4 immunoadhesin can be immobilized on a solid phase (e.g. on assay plates coated with goat-anti-human antibody). The ability of γ-HRG to bind to the immobilized immunadhesin can then be determined, e.g. by determining competitive displacement by other heregulin molecules. For more details, see the $^{125}$I-HRG binding assay described in the Example below.

As to property (b), the tyrosine phosphorylation assay using MCF7 cells described in the Example provides a means for screening for activation of ErbB receptors. In an alternative embodiment of the invention, the KIRA-ELISA described in WO 95/14930 can be used to qualitatively and quantitatively measure the ability of a γ-HRG variant to activate an ErbB receptor. Briefly, according to the assay described in this application, MCF7 cells (which produce measurable levels of ErbB2, ErbB3 and ErbB4) at cell densities of 60% to 75% confluency are added to each well in a flat-bottom-96 well culture plate and cultured overnight at 37° C. in 5% $CO_2$. The following morning the well supernatants are decanted, and the plates are lightly tamped on a paper towel. Media containing either culture medium (control), native sequence γ-HRG or variant γ-HRG is then added to each well. The cells are stimulated at 37° C. for about 30 min., the well supernatants are decanted, and the plates are once again lightly tamped on a paper towel. To lyse the cells and solubilize the receptors, 100 μl of lysis buffer is added to each well. Lysis buffer consists of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 μM leupeptin (ICN Biochemicals), and 2 mM sodium orthovanadate ($Na_3VO_4$, Sigma Chemical Co, St. Louis, Mo.), pH 7.5. The plate is then agitated gently on a plate shaker (Bellco Instruments, Vineland, N.J.) for 60 min. at room temperature.

While the cells are being solubilized, an ELISA microtiter plate (Nunc Maxisorp, Inter Med, Denmark) coated overnight at 4° C. with an affinity-purified polyclonal antibody directed against the ErbB2, ErbB3 or ErbB4 extracellular domain(depending on the receptor of interest) is decanted, tamped on a paper towel and blocked with 150 μl/well of Block Buffer (PBS containing 0.5% BSA (Intergen Company, Purchase, N.Y.) and 0.01% thimerosal) for 60 min. at room temperature with gentle agitation. After 60 minutes, the anti-ErbB coated plate is washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized ErbB receptor from the cell-culture microtiter well is transferred (85 μl/well) to an anti-ErbB coated and blocked ELISA well and is incubated for 2 h at room temperature with gentle agitation. The unbound receptor is removed by washing with wash buffer and 100 μl of biotinylated 4G10 (anti-phosphotyrosine antibody) in dilution buffer (PBS containing 0.5% BSA, 0.05% Tween-20, 5 mM EDTA, and 0.01% thimerosal), is added to each well. After incubation for 2 h at room temperature the plate is washed and 100 μl of HRPO-conjugated streptavidin (Zymed Laboratories, S. San Francisco, Calif.) in dilution buffer is added to each well. The plate is incubated for 30 minutes at room temperature with gentle agitation. The free avidin-conjugate is washed away and 100 μl freshly prepared substrate solution (tetramethyl benzidine (TMB); 2-component substrate kit; Kirkegaard and Perry, Gaithersburg, Md.) is added to each well. The reaction is allowed to proceed for 10 minutes, after which the color development is stopped by the addition of 100 μl/well 1.0 M $H_3PO_4$. The absorbance at 450 nm is read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

Thus, the degree of ErbB receptor phosphorylation induced by the variant γ-HRG can be compared to that induced by native sequence γ-HRG, as well as the control (presumably no activation).

Finally with respect to property (c), the ability of the γ-HRG variant to stimulate proliferation of a cell which expresses the ErbB2 and ErbB3 receptor and/or ErbB2 and ErbB4 receptor can readily be determined in cell culture. Useful cells for this experiment include MCF7 and SK-BR-3 cells obtainable from the ATCC. These tumor cell lines may be plated in cell culture plates and allowed to adhere thereto. The γ-HRG variant and native sequence γ-HRG control may be added at a final concentration of, e.g., 1 nM. Monolayers may be washed and stained/fixed with crystal violet. Proliferation can therefore be quantified as described. See the Example below for more details. Another useful cell for determining proliferation capacity of γ-HRG, including variants thereof, is the Schwann cell. See Li et al., supra.

2. Therapeutic Compositions and Methods

γ-HRG is also believed to be useful in promoting the development, maintenance, and/or regeneration of neurons in vivo, including central (brain and spinal chord), peripheral (sympathetic, parasympathetic, sensory, and enteric neurons), and motorneurons. Accordingly γ-HRG may be utilized in methods for the diagnosis and/or treatment of a variety of "neurologic diseases or disorders" which effect the nervous system of a mammal, such as a human.

Such diseases or disorders may arise in a patient in whom the nervous system has been damaged by, e.g., trauma, surgery, stroke, ischemia, infection, metabolic disease, nutritional deficiency, malignancy, or toxic agents. The agent is designed to promote the survival, proliferation or differentiation of neurons. For example, γ-HRG can be used to promote the survival or proliferation of motorneurons that are damaged by trauma or surgery. Also, γ-HRG can be used to treat motoneuron disorders, such as amyotrophic lateral sclerosis (Lou Gehrig's disease), Bell's palsy, and various conditions involving spinal muscular atrophy, or paralysis. γ-HRG can be used to treat human "neurodegenerative disorders", such as Alzheimer's disease. Parkinson's disease, epilepsy, multiple sclerosis, Huntington's chorea, Down's Syndrome, nerve deafness, and Meniere's disease.

Further, γ-HRG can be used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent.

γ-HRG may also be used to treat muscle cells and medical conditions affecting them. For example, the γ-HRG may be used to treat a pathophysiological condition of the musculature in a mammal, such as a skeletal muscle disease (e.g. myopathy or dystrophy), a cardiac muscle disorder (such as atrial cardiac arrhythmias, cardiomyopathy, ischemic damage, congenital disease, or cardiac trauma), or a smooth muscle disorder (for example, arterial sclerosis, vascular lesion, or congenital vascular disease); to treat muscle damage; to decrease atrophy of muscle cells; to increase muscle cell survival, proliferation and/or regeneration in a mammal; to treat hypertension; and/or to treat a muscle cell which has insufficient functional acetylcholine receptors (as in a patient with myasthenia gravis or tachycardia).

γ-HRG may be used to induce the formation of ion channels in a surface membrane of a cell and/or for enhancing the formation of synaptic junctions in an individual. γ-HRG may be also useful as a memory enhancer and may eliminate the "craving" for nicotine.

γ-HRG may be used to enhance repair and/or regeneration of tissues that produce ErbB receptor(s), especially the ErbB2 receptor. For example, γ-HRG may be used to treat dermal wounds; gastrointestinal disease; Barrett's esophagus; cystic or non-cystic end stage kidney disease; and inflammatory bowel disease. Similarly, this molecule may be used to promote reepithelialization in the human gastrointestinal, respiratory, reproductive or urinary tract.

In other embodiments, γ-HRG may be used to inhibit tumor cell invasion and mestasis. Tumors characterized by reduced endogenous γ-HRG levels (Park et al *Proc. Am. Assoc. Cancer Res.* 34:521 (1993)) may be responsive to γ-HRG. γ-HRG may be used to enhance chemotherapy by interacting with ErbB receptors and thereby enhancing tumor cell sensitivity to a chemotherapeutic agent. It may be desirable to treat carcinomas characterized by ErbB receptor overexpression using γ-HRG to direct a cytotoxic agent to the cancerous tissue. Examples of "cytotoxic agents" have been described above. γ-HRG-enzyme conjugates may be beneficial for targeted prodrug therapy for targeting cells expressing ErbB receptor(s).

In other situations, it may be desirable to treat the mammal with a γ-HRG antagonist, particularly where excessive levels of γ-HRG are present and/or excessive activation of ErbB receptors by γ-HRG is occurring in the mammal. Exemplary conditions or disorders to be treated with a γ-HRG antagonist include benign or malignant tumors (e.g. renal, liver, kidney, bladder, breast, gastric, ovarian, colorectal, prostate, pancreatic, ling, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; inflammatory, angiogenic and immunologic disorders; psoriasis and scar tissue formation. γ-HRG antagonists may also be used to reverse resistance of tumor cells to the immune-response, to inhibit pathological angiogenesis and to stimulate the immune system.

In still further embodiments of the invention, γ-HRG antagonists may be administered to patients suffering from neurologic diseases or disorders characterized by excessive production of γ-HRG and/or excessive ErbB receptor activation by γ-HRG. γ-HRG antagonist may be used in the prevention of aberrant regeneration of sensory neurons such as may occur post-operatively, or in the selective ablation of sensory neurons, for example, in the treatment of chronic pain syndromes.

For therapeutic uses, the γ-HRG protein may be administered to a patient in need thereof. Alternatively, gene therapy (either nucleic acid encoding γ-HRG or, where it is desired to inhibit γ-HRG, antisense polynucleotides) is contemplated herein.

Antisense inhibition of γ-HRG gene expression can occur at multiple levels. The prefered approach however, is one which involves interfering with translation of γ-HRG mRNA into protein. To achieve this, one may use an oligodeoxynucleotide (oligo) complementary to the γ-HRG mRNA. This antisense oligo binds by complementary Watson-Crick base pairing to the native sense mRNA. However, plasmid-derived antisense RNA (i.e. wherein the antisense DNA is provided in a plasmid) is also contemplated. Mercola and Cohen *Cancer Gene Therapy* 2(1):47–59 (1995). According to another embodiment, the so-called "anti-gene approach", the antisense molecule is one which binds to form a triple helix or triplex with γ-HRG DNA via Hoogsteen (or anti-Hoogsteen) hydrogen bonding of the third base in the antisense molecule with the already formed pair. Mercola and Cohen, supra. While antisense oligos can be directed anywhere along the γ-HRG mRNA transcript, the prefered target sequence is at the 5' end thereof, spanning the initiation codon. Generally, the antisense oligo will be relatively specific for γ-HRG and therefore is complementary to at least a portion of the DNA encoding the unique NTD of γ-HRG. Oligos of interest will normally comprise at least 15–17 bases. To identify the most active antisense sequence, deletion analysis may be performed.

Antisense oligos can be readily synthesized by automated methods. See U.S. Pat. No. 5,489,677 issued Feb. 6, 1996. Normally the antisense oligo intended for in vivo use will be modified so as to render it less susceptible to nuclease degradation and/or to improve the efficiency with which it is taken up by a cell. Several backbone modifications have been developed to counteract nuclease degradation. One exemplary modification results in a "methyl-phosphonate" (MO) oligo. According to this approach, one of the non-bridging oxygen atoms in the internucleotide bond is replaced with a methyl group which has the net effect of eliminating the negative charge of the oligo. Tonkinson et al. *Cancer Investigation* 14(1):54–65 (1996). Another modification described in Tonkinson et al. for reducing nuclease degradation is the phosphorothioate (PS) modification which involves replacing one of the nonbridging oxygens at the phosphorus with a sulfur. Other ways of modifying the basic oligo are reviewed in Cohen, *J. Adv. Pharmacol.* 25:319–339 (1993). For example, a new analog has been reported wherein the entire deoxyribose-phosphate backbone was replaced with a peptide-like backbone. See Mercola and Cohen supra. To improve cellular uptake, the antisense oligos can be encapsulated in liposomes, complexed with cationic lipids such as DOTMA, coupled to polylysine or lipofectin, and/or covalently attached to a cholesteryl moiety. See Tonkinson et al., supra.

There are two major approaches to getting the nucleic acid (optionally contained in a vector) into the patient's cells; in vivo and ex vivo. For in vivo delivery the nucleic acid is injected directly into the patient, usually at the site where the γ-HRG is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187).

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429–4432 (1987); and Wagner et al., *Proc. Natl. Acad. Sci. USA* 87:3410–3414 (1990). For review of the currently known gene marking and gene therapy protocols see Anderson et al., *Science* 256:808–813 (1992). See also WO 93/25673 and the references cited therein.

Therapeutic formulations of γ-HRG or γ-HRG antagonist are prepared for storage by mixing γ-HRG or γ-HRG antagonist having the desired degree of purity with optional physiologically acceptable carriers, excipients, or stabilizers (*Remington's Pharmaceutical Sciences*, 16th Edition, Osol., A., Ed., (1980)), in the form of lyophilized cake or aqueous solutions. Pharmaceutically acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™, or polyethylene glycol (PEG).

γ-HRG or γ-HRG antagonist to be used for in vivo administration must be sterile. This is readily accomplished by filtration through sterile filtration membranes, prior to or following lyophilization and reconstitution. The formulation ordinarily will be stored in lyophilized form or in solution.

Therapeutic γ-HRG or γ-HRG antagonist compositions generally are placed into a container having a sterile access port, for example, an intravenous solution bag or vial having a stopper pierceable by a hypodermic injection needle.

The route of γ-HRG or γ-HRG antagonist administration is in accord with known methods, e.g., injection or infusion by intravenous, intraperitoneal, intracerebral, intramuscular, intraocular, intraarterial, or intralesional routes, or by sustained-release systems as noted below. γ-HRG is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15:167–277 (1981) and Langer, *Chem. Tech.*, 12:98–105 (1982) or poly (vinylalcohol)), polylactides (U.S. Pat. No. 3,773,919, EP 58,481), copolymers of L-glutamic acid and gamma ethyl-L-glutamate (Sidman et al., *Biopolymers*, 22:547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133, 988).

Sustained-release γ-HRG or γ-HRG antagonist compositions also include liposomally entrapped drug. Liposomes containing γ-HRG are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal therapy. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent (such as Doxorubicin) is optionally contained within the liposome. See Gabizon et al. *J. National Cancer Inst.*81(19)1484 (1989).

For neurologic diseases or disorders, it may be desirable to adsorb γ-HRG onto a membrane, such as a silastic membrane, which can be implanted in proximity to damaged neural tissue, PCT Pub. No. WO 91/04014 (published Apr. 4, 1991).

Other therapeutic regimens may be combined with the administration of the γ-HRG or γ-HRG antagonist of the instant invention. For the treatment of neurological conditions, γ-HRG optionally is combined with or administered in concert with other neurotrophic factors to achieve a desired therapeutic effect. For example, γ-HRG may be used together with nerve growth factor (NGF), neurotrophins (NT-3), bone derived nerve factor (BDNF), neurotrophins-4 and -5 (NT-4/5), an insulin-like growth factor (e.g., IGF-1 or IGF-2), gas6, or another neurotrophic factor to achieve a synergistic stimulatory effect on neurons, wherein the term "synergistic" means that the effect of the combination of γ-HRG with a second substance is greater than that achieved with either substance used individually. Suitable dosages for the neurotrophic factors may be similar to those known in the art for such molecules.

The cancer patient to be treated with the γ-HRG or γ-HRG antagonist disclosed herein may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the γ-HRG or γ-HRG antagonist or may be given simultaneously therewith. For cancer indications, it may be desirable to also administer antibodies against tumor associated antigens, such as antibodies which bind to EGFR, ErbB2, ErbB3, ErbB4, or vascular endothelial factor (VEGF). Alternatively, or in addition, one or more cytokines may be co-administered to the patient.

An effective amount of γ-HRG or γ-HRG antagonist to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg of patient body weight or more per day, preferably about 10 μg/kg/day to 10 mg/kg/day. Typically, the clinician will administer γ-HRG or γ-HRG antagonist until a dosage is reached that achieves the desired effect for treatment of the above mentioned disorders.

3. Non-Therapeutic Methods

γ-HRG polypeptide can be used for growing cells (such as glial and muscle cells) ex vivo. It is desirable to have such populations of cells in cell culture for isolation of cell-specific factors e.g. $P75^{NGFR}$ which is a Schwann cell specific marker. Such factors are useful as diagnostic tools or, in the case of $P75^{NGFR}$, can be used an antigens to generate antibodies for diagnostic use. It is also beneficial to have populations of mammalian cells (e.g. Schwann cells) for use as cellular prostheses for transplantation into mammalian patients (e.g. into areas of damaged spinal cord in an effort to influence regeneration of interrupted central axons, for assisting in the repair of peripheral nerve injuries and as alternatives to multiple autografts).

In accordance with the in vitro methods of the invention, cells comprising an ErbB receptor are provided and placed in a cell culture medium. Suitable tissue culture media are well known to persons skilled in the art and include, but are not limited to, Minimal Essential Medium (MEM), RPMI-1640, and Dulbecco's Modified Eagle's Medium (DMEM). These tissue culture medias are commercially available from Sigma Chemical Company (St. Louis, Mo.) and GIBCO (Grand Island, N.Y.). The cells are then cultured in the cell culture medium under conditions sufficient for the cells to remain viable and grow in the presence of an effective amount of γ-HRG. The cells can be cultured in a variety of ways, including culturing in a clot, agar, or liquid culture.

The cells are cultured at a physiologically acceptable temperature such as 37° C., for example, in the presence of an effective amount of γ-HRG. The amount of γ-HRG may vary, but preferably is in the range of about 10 ng/ml to about 1 mg/ml. The γ-HRG can of course be added to the culture at a dose determined empirically by those in the art without undue experimentation. The concentration of γ-HRG in the culture will depend on various factors, such as the conditions under which the cells and γ-HRG are cultured. The specific temperature and duration of incubation, as well as other culture conditions, can be varied depending on such factors as, e.g., the concentration of the γ-HRG, and the type of cells and medium. Those skilled in the art will be able to determine operative and optimal culture conditions without undue experimentation.

Techniques for culturing Schwann cells ex vivo are described in Li et al., supra and Sklar et al., supra describe ex vivo culturing of clonal human myoblasts. γ-HRG can replace the other heregulin polypeptides used in these methods.

γ-HRG polypeptide can be used in the diagnosis of cancers characterized by erbB (e.g. erbB2) overexpression and/or amplification. Similarly, molecules which detect γ-HRG expression (e.g. nucleic acid probes and anti-γ-HRG antibodies) can be used to detect γ-HRG expression (e.g. in cancer where γ-HRG leads to the formation of a constitutive active complex, such as some breast cancers, see Example below). Such diagnostic assay(s) can be used in combination with other diagnostic/prognostic evaluations such as determining lymph node status, primary tumor size, histologic grade, estrogen or progesterone status, tumor DNA content (ploidy), or cell proliferation (S-phase fraction). See Muss et al., *New Eng. J. Med.*, 330(18):1260–1266 (1994).

The sample as herein defined is obtained, e.g. tissue sample from the primary lesion of a patient. Formalin-fixed, paraffin-embedded blocks are prepared. See Muss et al., supra and Press et al., *Cancer Research* 54:2771–2777 (1994). Tissue sections (e.g. 4 μM) are prepared according to known techniques. The extent of γ-HRG binding to the tissue sections is then quantified.

Generally, the γ-HRG (protein or nucleic acid probe) or HRG antibody will be labelled either directly or indirectly with a detectable label. Numerous labels are available which can be generally grouped into the following categories:

(a) Radioisotopes, such as $^{35}S$, $^{14}C$, $^{125}I$, $^{3}H$, and $^{131}I$. The γ-HRG or antibody can be labeled with the radioisotope using the techniques described in *Current Protocols in Immunology*, Ed. Coligen et al., Wiley Publishers, Vols 1 & 2, for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the γ-HRG or antibody using the techniques disclosed in *Current Protocols in Immunology*, supra, for example. Fluorescence can be quantified using a fluorimeter (Dynatech).

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to proteins are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147–166 (1981) and *Current Protocols in Immunology*, supra.

Examples of enzyme-substrate combinations include, for example: (a) Horseradish peroxidase (HRPO) with hydrogen peroxidase as a substrate, wherein the hydrogen peroxidase oxidizes a dye precursor (e.g. orthophenylene diamine (OPD) or 3,3′,5,5′-tetramethyl benzidine hydrochloride (TMB)); (b) alkaline phosphatase (AP) with para-Nitrophenyl phosphate as chromogenic substrate; and (c)β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the γ-HRG or antibody. The skilled artisan will be aware of various techniques for achieving this. For example, the γ-HRG or antibody can be conjugated with biotin and any of the three broad categories of labels mentioned above can be conjugated with avidin, or vice versa. Biotin binds selectively to avidin and thus, the label can be conjugated with the γ-HRG or antibody in this indirect manner. See, *Current Protocols in Immunology*, supra, for a review of techniques involving biotin-avidin conjugation. Alternatively, to achieve indirect conjugation of the label with the γ-HRG or antibody, the γ-HRG or antibody is conjugated with a small hapten (e.g. digoxin) and one of the different types of labels mentioned above is conjugated with an anti-hapten antibody (e.g. anti-digoxin antibody). Thus, indirect conjugation of the label with the γ-HRG or antibody can be achieved.

In another embodiment of the invention, the γ-HRG or antibody need not be labeled, and the presence thereof can be detected using a labeled anti-γ-HRG or anti-antibody antibody (e.g. conjugated with HRPO).

In the preferred embodiment, the γ-HRG or antibody is labeled with an enzymatic label which catalyzes a color change of a substrate (such as tetramethyl benzimidine (TMB), or orthaphenylene diamine (OPD)). Thus, the use of radioactive materials is avoided. A color change of the reagent can be determined spectrophotometrically at a suitable wavelength (e.g. 450 nm for TMB and 490 nm for OPD, with a reference wavelength of 650 nm).

Thus, the tissue sections on slides are exposed to the labelled γ-HRG or antibody and the intensity of staining of the tissue sections is determined. While in vitro analysis is normally contemplated, in vivo diagnosis using γ-HRG or antibody conjugated to a detectable moiety (e.g. In for imaging) can also be performed. See, e.g., U.S. Pat. No. 4,938,948.

γ-HRG preparations are also useful as standards in assays for γ-HRG (e.g., by labeling γ-HRG for use as a standard in a radioimmunoassay, enzyme-linked immunoassay, or radioreceptor assay), in affinity purification techniques (e.g. for an ErbB receptor such as ErbB3 or ErbB4 receptor), and in competitive-type receptor binding assays when labeled with radioiodine, enzymes, fluorophores, spin labels, and the like. γ-HRG polypeptides are also useful as immunogens for generating anti-γ-HRG antibodies for diagnostic use. In this respect the unique NTD (or fragments thereof, (e.g., having a consecutive sequence of 20 or more amino acid residues) are useful as immunogens for generating γ-HRG-specific antibodies for use in its detection and/or purification.

Similarly, the nucleic acid encoding γ-HRG is useful as a probe for detecting γ-HRG expression in various tissues. In this respect, nucleic acid encoding or complementary to nucleic acid encoding the unique NTD of γ-HRG or a fragment thereof is particularly useful. Techniques for DNA analysis are well known. See, e.g. U.S. Pat. No. 4,968,603. Normally, the DNA analysis will involve Southern blotting a sample derived from a mammal.

4. γ-HRG Antibodies & Uses Thereof

Techniques for generating antibodies, such as polyclonal and monoclonal antibodies are well known in the art. Polyclonal antibodies generally are raised by immunizing animals with γ-HRG or a fragment thereof (optionally conjugated to a heterologous protein that is immunogenic in the species to be immunized). Monoclonal antibodies directed toward γ-HRG may be produced using any method which provides for the production of antibody molecules by continuous cell lines in culture. Examples of suitable methods for preparing monoclonal antibodies include the original hybridoma method of Kohler et al., *Nature* 256:495–497 (1975), and the human B-cell hybridoma method, Kozbor, J., *Immunol.* 133:3001 (1984); Brodeur et al., *Monoclonal Antibody Production Techniques and Applications*, pp.51–63 (Marcel Dekker, Inc., New York, 1987); and Boerner et al., *J. Immunol.* 147:86–95 (1991).

DNA encoding the monoclonal antibodies of the invention is readily isolated and sequenced using conventional procedures (e.g., by using oligonucleotide probes that are capable of binding specifically to genes encoding the heavy and light chains of antibodies). The hybridoma cells of the invention serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (Morrison, et al., *Proc. Natl. Acad. Sci. USA* 81:6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of an anti-γ-HRG monoclonal antibody herein.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321:522–525 (1986); Riechmann et al., Nature 332:323–327 (1988); and Verhoeyen et al., Science 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol, 151:2296 (1993); and Chothia and Lesk, J. Mol. Biol. 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA 89:4285(1992); and Presta et al., J. Immnol. 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

According to an alternative method for producing human antibodies, transgenic animals (e.g., mice) are available that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature 362:255–258 (1993); and Bruggermann et al., Year in Immuno. 7:33 (1993).

Alternatively, phage display technology (McCafferty et al., Nature 348:552–553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g., Johnson, Kevin S. and Chiswell, David J., Current Opinion in Structural Biology 3:564–571 (1993). Several sources of V-gene segments can be used for phage display. Clackson et al., Nature, 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581–597 (1991), or Griffith et al., EMBO J. 12:725–734 (1993).

Bispecific antibodies are antibodies that have binding specificities for at least two different antigens. In the present case, one of the binding specificities is for a γ-HRG, the other one is for any other antigen, e.g., for another polypeptide that activates an ErbB receptor. For example, bispecific antibodies specifically binding γ-HRG and another heregulin polypeptide are within the scope of the present invention. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175:217–225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing erbB and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. *Proc. Natl. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al. *J. Immunol.* 152:5368 (1994).

Antibodies with more than two valencies are contemplated. For example, trispecific antibodies can be prepared. Tutt et al. *J. Immunol.* 147: 60 (1991).

To manufacture a neutralizing antibody, antibodies are made using the techniques for generating these molecules elaborated above. The preferred neutralizing antibody is specific for γ-HRG (i.e. does not significantly cross-react with other heregulins as determined by immuno-precipitation, for example). Following production of a panel of antibodies, the antibodies are subjected to a screening process in order to identify those molecules which meet the desired criteria (i.e. which are able to neutralize a biological activity of γ-HRG either in vitro or in vivo). For example, the ability of the γ-HRG to block γ-HRG activity in any one or more of the assays described above for screening for γ-HRG variants can be evaluated. Those antibodies which block the ability of γ-HRG to bind to and/or activate an ErbB receptor and/or the mitogenic activity of γ-HRG on cells can be selected as neutralizing antibodies.

The antibodies may be coupled to a cytotoxic agent or enzyme (e.g. a prodrug-activating enzyme) in a similar manner to that described above for γ-HRG polypeptide. Furthermore, the antibodies may be labelled as described above for γ-HRG polypeptides, especially where the antibodies are to be used in diagnostic assays.

γ-HRG antibodies are useful in diagnostic assays for γ-HRG, e.g., its production in specific cells, tissues, or serum. The antibodies are labeled in the same fashion as γ-HRG described above and/or are immobilized on an insoluble matrix. Suitable diagnostic assays for γ-HRG antibodies are well known an have been discussed above with respect to γ-HRG polypeptide assays. Given the secreted nature of the γ-HRG molecule, a particularly useful assay for detecting this molecule in biological fluids is as described in U.S. Pat. No. 5,401,638, issued Mar. 28, 1995. According to this approach, the γ-HRG in the bodily fluid (e.g. human plasma or serum) is "captured" using an immobilized antibody which binds specifically thereto. A second antibody, which is optionally labelled, is then used to detect the captured γ-HRG. This second antibody may be one which binds any epitope of the γ-HRG. Thus, the amount of γ-HRG in the bodily fluid relative to a control can be detected.

γ-HRG antibodies are also useful for affinity purification of γ-HRG from recombinant cell culture or natural sources.

Neutralizing anti-γ-HRG antibodies may also be used to block γ-HRG biological activity in vitro or in vivo. Clinical situations in which this may be desirable are discussed above with respect to uses for γ-HRG antagonists.

5. Diagnostic Kits & Articles of Manufacture

Since the invention provides at least two types of diagnostic assay (i.e. for detecting cancer using γ-HRG and for detecting the presence of γ-HRG in a sample using antibodies or DNA markers) as a matter of convenience, the reagents for these assays can be provided in a kit, i.e., a packaged combination of reagents, for combination with the sample to be tested. The components of the kit will normally be provided in predetermined ratios. Thus, a kit may comprise the antibody or γ-HRG (DNA or polypeptide) labelled directly or indirectly with a suitable label. Where the detectable label is an enzyme, the kit will include substrates and cofactors required by the enzyme (e.g. a substrate precursor which provides the detectable chromophore or fluorophore). In addition, other additives may be included such as stabilizers, buffers and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the bioassay.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is γ-HRG or an antagonist thereof. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered by way of illustration and not by way of limitation. The disclosures of all citations in the specification are expressly incorporated herein by reference.

EXAMPLE 1

This example describes the isolation and biochemical characterization of the γ-HRG polypeptide of the present invention.

Materials & Methods

Reagents: The EGF-like domain of HRGβ1$_{(177-244)}$ was expressed in *E. coli*, purified and radioiodinated as described previously (Sliwkowski et al. *J. Biol. Chem.* 269:14661–14665 (1994)). The anti-ErbB2 monoclonal antibodies 2C4 and 4D5 have been described elsewere (Fendly et al. *Cancer Research* 50:1550–1558 (1990)).

ErbB3- and ErbB4-immunoadhesins: A unique MI I site was engineered into a plasmid expressing human IgG heavy chain at the region encoding the hinge domain of the immunoglobulin. MI I sites were also engineered into a set of ErbB expression plasmids at the region encoding the ECD/TM junctions of these receptors. All mutageneses were done using the Kunkel method (Kunkel, T., *Proc. Natl. Acad. Sci. U.S.A.* 82:488 (1985)). The MI I sites were utilized to make the appropriate ErbB-IgG fusion constructs. The fusion junctions of the various ErbB-IgG chimeras were: for ErbB2, $E^{646}_{ErbB2}$-(TR)-DKTH$^{224}_{VH}$; for ErbB3, $L^{636}_{ErbB3}$-(TR)-DKTH$^{224}_{VH}$; for ErbB4, $G^{640}_{ErbB4}$-(TR)-DKTH$^{224}_{VH}$. The conserved TR sequence is derived from the MI I site. The final expression constructs were in a pRK-type plasmid backbone wherein eukaryotic expression is driven by a CMV promoter (Gorman et al., *DNA Prot. Eng. Tech.* 2:3–10 (1990)).

To obtain protein for in vitro experiments, adherent HEK-293 cells were transfected with the appropriate expression plasmids using standard calcium phosphate methods (Gormar et al., supra and Huang et al., *Nucleic Acids Res.* 18:937–947 (1990)). Serum-containing media was replaced with serum-free media 15 hours post-transfection and the transfected cells incubated for 5–7 days. The resulting conditioned media was harvested and passed through Protein A columns (1 mL Pharmacia HiTrap™). Purified IgG fusions were eluted with 0.1 M citric acid (pH 4.2) into tubes containing 1 M Tris pH 9.0. The eluted proteins were subsequently dialyzed against PBS and concentrated using Centri-prep-30 filters (Amicon). Glycerol was added to a final concentration of 25% and the material stored at −20° C. Concentrations of material were determined via a Fc-ELISA.

Cell Culture: Human breast cancer cell lines MDA-MB-175, MDA-MB-231, SK-BR-3 and MCF7 were obtained from the American Type Culture Collection and maintained in a 50:50 mixture of F12 Ham's and Dulbecco's modified Eagle medium (DMEM), supplemented with 10% heat inactivated FBS, 2 mM glutamine and 10% penicillin-streptomycin.

Generation and Characterization of cDNA Library: Total RNA was purified from MDA-MB-17 cells using the guanidinium isothiocyanate-cesium chloride procedure (Sambrook et al., *Molecular Cloning: A Laboratory Manual* (New York: Cold Spring Harbor Laboratory Press, (1989)). Poly (A)$^+$ RNA was isolated using oligo (dT) Dynabeads (DYNAL) as recommended by the supplier. First and second strand syntheses were performed using a Gibco BRL cDNA synthesis kit. λgt10 cDNA recombinants were generated when a cDNA cloning system from Amersham was used. In vitro packaging was performed using Gigapack II™ packaging extract (Stratagene). PstI-XhoI HRGβ3 cDNA fragment (nt 144–618) was labeled by random priming and 1×10$^6$ plaques were screened. Positive clones were confirmed and purified by secondary and tertiary screening. Phage DNA was isolated as a BamHI fragment and subcloned into the corresponding site of pBluescript SK⁻. Clone 5 was completely sequenced using the Sequenase version 2.0™ DNA sequencing kit (United States Biochemicals, Inc.). Both strands were sequenced.

Bacterial Expression System: A cDNA fragment of clone 5 (nt 1690–2722) was subcloned into the pET-32 TRX fusion vector (Novagen). This BglII-BglII fragment was inserted into the BamHI site of the pET32a plasmid. The trxγ-HRG (amino acids 455–768) protein expression in $E.$ $coli$ was induced as recommended by the supplier.

Purification of Recombinant γ-HRG: $E.coli$ cells expressing trxγ-HRG were collected and suspended at 9 ml/g in 50 mM Tris HCL pH 8. Lysozyme was added to a final concentration of 0.2 mg/ml and the solution was stirred on ice for 1 hr. Dnase I (10 μg/ml) and $MgCl_2$ (4 mM) were added. The solution was then sonicated for 30 min and cell pellets collected afterwards. The pellet fraction was dissolved at 250 ml/g in 6 M Gdn HCL, 0.1 M Tris HCL, pH 8.8. Solubilized proteins were sulfitolyzed by adding ¹⁄₁₀ volume of 1 M $Na_2SO_3$ and ¹⁄₁₀ volume of 0.2 M $Na_2S_4O_6$. The reaction was allowed to proceed for 1.5 hours at room temperature and protein was purified by gel filtration chromatography using a High Load Superdex™ 75 prep grade column (Pharmacia). Refolding was initiated by the addition of 1 mM cysteine, and 10 mM methionine was added as an antioxidant and incubated overnight at room temperature. Protein concentration was determined by quantitative amino acid analysis.

Northern and Southern Hybridization: Total RNA was isolated by the method of Chomczynski et al. $Anal Biochem.$ 162:156–159 (1987). Poly (A)⁺ was isolated using oligo d(T) cellulose columns (Qiagen) as recommended by the supplier. RNA was denatured and size fractioned in a 0.8% formaldehyde/1% agarose gel and transferred onto nylon membrane (Hybond, Amersham). RNA was UV crosslinked (UV Stratalinker, Stratagene). Prehybridization was carried out at 42° C. in 50% formamide/1% SDS/1 M NaCl, 10% dextransulfate and 100 μg/ml herring sperm DNA for at least 2 hours. cDNA probes using either a restriction fragment with complementary sequence to the EGF-like domain of HRGβ3 or a KpnI-AvaII cDNA fragment encoding the unique sequence of γ-HRG (nt 1238–1868) were radiolabeled by random priming (Prime-It II, Stratagene). Hybridization was done in equal solution at 42° C. containing the ³²P labeled fragments for 16 hr. Blots were washed several times with 2×SSC/1% SDS at room temperature, washed with the same solution at 65° C. for 20 min and finally washed with 0.2×SSC/0.1% SDS at room temperature for 15 min. The blots were air dried and exposed to Du Pont Reflection™ film with intensifying screens at −80° C. for 7–40 hours. Human multiple tissue Northern blots (Clontech) containing 2 μg poly (A)⁺ from spleen, thymus, prostate, testis, ovary, small intestine, colon, peripheral blood leukocytes, heart, brain, placenta, lung, liver, skeletal muscle, kidney and pancreas were hybridized with a radiolabeled γ-HRG cDNA probe (nt 841–1447) as recommended by the supplier.

MDA-MB-175 and MDA-MB-231 genomic DNA was isolated as described in Sambrook et al, supra. DNA was digested with different restriction enzymes, prior to transfer treated with 0.25 N HCl and transferred onto nylon membrane (Hybond, Amersham). BglII-NdeI cDNA fragment of γ-HRG (nt 1690–2351) was also radiolabeled by random priming and used as a hybridization probe. Prehybridization was carried out in 6×SSC/5×Denhardt's/0.75% SDS, 10% Dextransulfate and 100 μg/ml herring sperm DNA at 68° C. for 4 hours and hybridization with radiolabeled probe was done overnight. The same wash conditions as for Northern blots were used except a wash step with 0.2×SSC/0.1% SDS at 68° C. was added and detection was pursued as described above.

¹²⁵I-HRG Binding Assay. Binding assays were performed in Nunc breakapart strip wells. Plates were coated at 4° C. overnight with 100 μl of 5 μg/ml goat-anti-human antibody (Boehringer Mannheim) in 50 mM carbonate buffer (pH 9.6). Plates were rinsed twice with wash buffer (PBS/0.05% Tween-20™) and blocked with 100 μl 1% BSA/PBS for 30 min. Buffer was removed and each well was incubated with 15 ng IgG fusion protein in 1% BSA/PBS under vigorous shaking for 1.5 hours. Plates were rinsed three times with wash buffer and competitive binding was carried out by adding various amounts of γ-HRG and ¹²⁵I-HRGβ1 under vigorous shaking. After incubation for 1.5–2 hours, wells were rinsed three times with wash buffer, drained and individual wells were counted using a 100 Series Iso Data γ-counter.

Tyrosine Phosphorylation Assay. MCF7 cells were plated in 24 well plates at $1\times10^5$ cells/well in F12/DMEM containing 10% FBS. After 48 hours, cells were washed with serum free F12/DMEM and serum starved for 6 hours. Various concentrations of bacterial expressed truncated γ-HRG (i.e., 0 pM, 22 pM, 66 pM, 200 pM and 600 pM trxγ-HRG) or unpurified conditioned medium of MDA-MB-175 cells were prepared in binding buffer (0.1% BSA in F12/DMEM) and added to each well. After 8 min incubation at room temperature, media was carefully aspirated and reactions were stopped by adding 100 μl of sample buffer (5% SDS, 0.25% 2-mercaptoethanol, 25 mM Tris-HCL pH 6.8). 20 μl of each sample was size fractionated in a 4–12% gradient gel (Novex) and then electrophoretically transfered onto nitrocellulose membrane. Antiphosphotyrosine (4G10, from UBI, used at 1 μg/ml) immunoblots were developed and the predominant reactive band at $M_r$~180 kDa was quantified by reflectance densitometry.

Production and characterization of conditioned medium from MDA-MB-175 cells. Cells were seeded in T175 flasks and grown until reaching 70–80% confluency (~$2.5\times10^7$ cells/flask). Subsequently, cells were washed with PBS and grown in serum free F12/DMEM medium for 3–4 days. Medium was then collected, filtered and concentrated using an ultrafiltration cell with YM10 Diaflo ultafiltration membranes (Amicon). γ-HRG was visualized in conditioned medium of MDA-MB-175 cells by Western blot analysis under non reducing conditions. γ-HRG was partially purified by HPLC using a C4 reverse phase column. CHO expressed full length HRGβ1 (lane 1) and semi pure γ-HRG (lane 2) were electrophoresed, blot was probed with ErbB2/ErbB4 IgG heterodimers and Western blot was developed. A ~64 kDa band could be seen in the lane containing partial purified supernatant whereas CHO expressed full length HRGβ1 migrated as a 45 kDa protein.

Cell Proliferation Assay with Crystal Violet: Tumor cell lines were plated in 96 well plates at following densities: $2\times10^4$ cells/well for MDA-MB-175 and $1\times10^4$ cells/well for SK-BR-3. The media contained 1% FBS and cells were allowed to adhere for 2 hours. Monoclonal antibodies, immunoadhesions (10 μg/ml) or media alone were added and the cells were incubated for 2 hours at 37° C. rHRGβ1₁₇₇₋₂₄₄ was added at a final concentration of 1 nM, or 100 nM for neutralising the immunoadhesion, and the cells were incubated for 4 days. Monolayers were washed with PBS and stained/fixed with 0.5% crystal violet. Plates were air dried, the dye was eluted with 0.1 M sodium citrate (pH 4.2) in ethanol (50:50) and the absorbance was measured at 540 nm.

Results & Discussion

Isolation and sequence analysis of γ-HRG: To characterize the heregulin transcript in MDA-MB-175 cells, a λgt 10 cDNA library was constructed with mRNA derived from this cell line. The library was screened with a cDNA probe corresponding to the EGF-like domain and part of the N-terminal sequence of HRGβ3. Various clones were identified. One of the clones which appeared to contain the full length cDNA sequence was isolated and sequenced. FIG. 1 shows the nucleotide sequence and the predicted amino acid sequence of γ-HRG. The single open reading frame of 2303 bp starts with an ATG codon at nt 334. This start codon lies in a nucleotide sequence context, which is known to be a potential translation initiation site (Kozak, *Nucleic Acid Research* 15:8125–8148 (1987)). Several termination codons were found upstream of the initiation codon. The stop codon TAG at nt 2637 is followed by the 3' noncoding sequence, which is identical to other HRG isoform sequences and includes a polyadenylation signal followed by an A-rich region. The open reading frame encodes a protein of 768 amino acid residues with a calculated molecular mass of 84.2 kDa.

Structural analysis of γ-HRG: γ-HRG as shown in FIG. 2 has an EGF-like domain which is completely identical to GGF, SMDF and the HRGβ isoforms. Like GGF, SMDF and HRGβ3 the amino acid sequence ends in the juxtamembrane region after a stretch of 11 variable amino acid residues. Therefore γ-HRG lacks the transmembrane region and the cytoplasmic domain. As in HRGα and HRGβ, the spacer region with many potential N-and O-linked glycosylation sites is present. This region connects the EGF-like domain with the Ig-like domain. Except for the recently discovered new isoform, named sensory and motor neuron derived factor (SMDF), all known HRG forms contain this motif. The N-terminal region upstream of the Ig-like domain is unique and distinct from all other heregulins. The first 33 amino acids which are found in HRGα and HRGβ are absent. Instead γ-HRG possesses a 560 amino acid sequence, which shows no similarity to any known DNA or protein sequences. As seen with other HRG isoforms, γ-HRG lacks an N-terminal signal sequence. However, the unique region shows a 22 amino acid stretch of hydrophobic amino acid residues, which may function as an internal signal sequence and may be responsible for the secretion ability of γ-HRG. No structural motifs could be found in the N-terminal region after searching a motif database.

Identification of heregulin transcripts in MDA-MB-175, MDA-MB-231 cell lines and different human tissues: To compare the heregulin transcripts in MDA-MB-175, MDA-MB-231 cell lines and mammary gland tissue, a Northern blot analysis was performed on poly(A)$^+$ RNA. By using a radiolabeled fragment corresponding to the EGF-like domain of HRGβ3, three transcripts were detected in MDA-MB-231 RNA as observed before (Holmes et al., *Science* 256:1205–1210 (1992)). The variability in signal intensities of the three transcripts is due to different cell batches and RNA preparations. The same transcript sizes were also seen in normal breast tissue RNA. However in MDA-MB-175 RNA only one major transcript of 3.3 kb could be found. When a $^{32}$P labeled cDNA probe corresponding to the unique N-terminal sequence of γ-HRG was used, no hybridization signals could be located either in MDA-MB-231 RNA nor in breast tissue RNA. In MDA-MB-175 RNA again the major 3.3 kb band could be detected. Due to the overexposure of the autoradiogram, bands of much lower intensities with the sizes of 1.8 kb, 5 kb and 7.5 kb could be seen. They were also present in autoradiograms after extensive exposure using the EGF-like domain probe. Various human tissues were examined for the presence of γ-HRG mRNA. Transcripts were found in testis, ovary, skeletal muscle and in lower intensity in heart, brain and kidney. No transcripts could be found by Northern blot analysis in spleen, thymus, prostate, small intestine, colon, peripheral blood leukocytes, placenta, lung, liver and pancreas. The mRNA in the expressing tissues varied by sizes. Without being bound to any theory, this is probably due to differential splicing events in these tissues.

The γ-HRG isoform is not a result of DNA rearrangement: The heregulin/NDF isoforms are products of a differentially spliced gene. The possibility that γ-HRG may not be an alternative splice variant of the heregulin gene, but a product of DNA rearrangement in MDA-MB-175 cells was addressed. To answer this question, Southern blot analysis of genomic DNA retrieved from MDA-MB-231 and MDA-MB-175 cells was performed. Genomic DNA of both cell lines was digested with restriction enzymes and fractionated by size. The blot was hybridized with a radiolabeled cDNA probe (nt 1690–2351) of γ-HRG. The 5' prime of the cDNA probe was complementary to the unique N-terminal sequence. The 3' prime contained a part of the commonly shared sequence of the heregulins, which Marchionni et al. supra defined as exon 2. This means that the probe was designed over the exon/intron junction or possible DNA rearrangement site. Comparison of the band sizes in both MDA-MB-175 and MDA-MB-231 cell lines revealed no differences, which is a strong indication that γ-HRG is not a product of DNA rearrangement, but rather a new splice variant of the heregulin gene.

Functional activity of γ-HRG. When medium conditioned by MDA-MB-175 cells was analyzed in a binding assay on MCF7 cells a concentration of ~26 pM could be detected. However this number was obtained by comparing the displacement characteristics of unpurified medium to HRGβ1$_{(177-244)}$ binding. Due to this low concentration in the supernatant, the recombinant protein was produced. Partial sequence analysis of different λgt 10 clones, obtained after screening with the EGF-like domain, led to the conclusion that MDA-MB-175 cells transcribe more than one novel HRG isoform. Aside from γ-HRG of FIG. 1 (SEQ ID NO:2), clone 20 encoding an isoform of the FIG. 1 γ-HRC sequence was extensively characterized (see FIGS. 5 and 6A–G; SEQ ID NOS. 10 and 11, respectively). Compared to the γ-HRG sequence, clone 20 contains at least one insert of 26 amino acid residues between amino acid 560 and 561. Furthermore the N-terminal DNA sequence varies from γ-HRG by additional base pairs. However clone 20 lacks the 5' end. Initial expression experiments in mammalian cells were done with a construct containing clone 20 DNA sequence. Protein sequence analysis of the secreted form showed a processed polypeptide, lacking the N-terminal sequence and hydrophobic region. Proteolytic cleavage occured in the additional insert region of this clone between two arginine residues (i.e. the N-terminal residue of the proteolytically processed protein was residue 315 in FIG. 5; SEQ ID NO: 10). Based on these data, a N-terminal truncated version of γ-HRG thioredoxin fusion protein was expressed in an bacterial expression system. Although it has been reported that several mammalian cytokines and growth factors stay soluble in the *E.coli* cytoplasm, when expressed as a C-terminal thioredoxin fusion protein, trxγHRG was insoluble (La Vallie et al.

Bio/Technology 11:187–193 (1993)). Under those conditions trxγ-HRG accumulated in inclusion bodies from which the recombinant protein was isolated. Following purification, the protein was sulfitolyzed and then refolded by the addition of cysteine. The interaction of γ-HRG with the heregulin receptors ErbB3 and ErbB4 was examined. Binding analysis was performed using an in vitro system, so that the binding characteristics of the individual receptors could be studied. IgG fusion proteins containing the extracellular domain of ErbB3 or ErbB4 were constructed. The imunoadhesins were incubated with $^{125}$I-HRGβ1(177–244) (0.23 nM) and increasing amounts of unlabeled γ-HRG. γ-HRG was able to displace $^{125}$I-HRGβ1$_{(177-244)}$ binding to both receptors respectively ErbB3 and ErbB4. Binding analysis revealed an $EC_{50}$ of 19±1.3 nM for γ-HRG to ErbB3 immunoadhesins and an $EC_{50}$ of 13.3±0.8 nM to ErbB4-IgG (FIG. 3). A comparison of HRGβ1$_{(177-244)}$ and the thioredoxin HRGβ1$_{(177-244)}$ fusion protein in a competitive binding assay showed that the N-terminal thioredoxin sequence did not affect binding affinity. The ability of γ-HRG to stimulate tyrosine phosphorylation of ErbB receptor(s) in the human breast cancer cell line MCF7, which expresses all tyrosine kinase class I receptors in moderate levels (Beerli et al. *Mol. Cell. Biol.* 15:6496–6505 (1995)), was investigated. Cells were treated with various amounts of γ-HRG and tyrosine kinase activity was determined using immunoblotting with anti-phosphotyrosine antibody. Dose dependent tyrosine phosphorylation could be detected. The $EC_{50}$ was similar to the one seen in MCF7 cells treated with HRGβ1 (60 pM). The functional activity of γ-HRG found in the supernatant of MDA-MB-175 cells was evaluated. The size determination of the secreted isoform was carried out by Western blot performed with a ErbB2/ErbB4-IgG heterodimer. γ-HRG was semi-purified from conditioned medium by HPLC using a C4 reverse phase column. By SDS-PAGE, a ~64 kDa band was seen, whereas CHO expressed full length HRGβ1 migrated with a molecular weight size of 45 kDa. These data indicate that the mature protein is 20 kDa greater than HRGβ1. Without being bound to any one theory, processing of γ-HRG may have occurred during the secretion event so as to release the "mature" form of γ-HRG. Binding studies on MCF7 cells revealed a dose dependent displacement of $^{125}$I-HRGβ1$_{(177-244)}$ with unpurified conditioned medium. Furthermore tyrosine phosphorylation studies on MCF7 cells also showed signaling capability of secreted γ-HRG. These findings are in agreement with the data obtained from experiments carried out with recombinant γ-HRG.

Heregulin is an autocrine growth factor for the human breast tumor cell line MDA-MB-175; MDA-MB-175 cells were treated with an ErbB2 monoclonal antibody (2C4) that interferes with the ligand dependent formation of ErbB2/ErbB3 and ErbB2/ErbB4 heterodimer complexes Sliwkowski et al., *J. Biol. Chem.* 269:14661–14665 (1994). In a crystal violet staining assay, incubation with 2C4 showed a strong growth inhibitory effect on this cell line (FIG. 4A). Exogenous HRG did not significantly reverse this inhibition. On the other hand 2C4 revealed no inhibitory effect on the ErbB2 overexpressing cell line SK-BR-3 (FIG. 4B). Treatment with 4D5, another monoclonal antibody against ErbB2 which interacts with a different epitope from 2C4 (Fendly et al., supra), was moderate growth inhibitory in MDA-MB-175 cells. Inhibition of cell proliferation by 4D5 is dependent on the ErbB2 expression level (Lewis et al. *Cancer Immunol. Immunother.* 37:255–263 (1993)). A maximum inhibition of 66% in SK-BR-3 cells could be detected (FIG. 5B). However this effect could be overcome by exogenous HRG. To further verify that secreted γ-HRG interacts with ErbB receptors in an autocrine manner, additional inhibition experiments were performed using soluble receptor immunoadhesins. MDA-MB-175 and SK-BR-3 cells were incubated with ErbB4-IgG for4 days and cell proliferation was measured by crystal violet staining. Treatment with the immunoadhesin resulted in a strong growth inhibition of 64% in MDA-MB-175 cells. This effect was completely neutralized by adding excess exogenous HRG. In SK-BR-3 cells, which do not express HRG, the ErbB4-IgG treatment was ineffective. From these findings, it was concluded that the secretion of γ-HRG by MDA-MB-175 leads to the formation of a constitutive active receptor complex and stimulates the growth of these cells in an autocrine manner.

What is claimed is:

1. An isolated antibody which binds to γ-HRG N-terminal domain (NTD) of SEQ ID NO:4.

2. The antibody of claim 1 which is a neutralizing antibody.

3. A method for detecting γ-HRG comprising contacting a sample suspected of containing γ-HRG with the antibody of claim 1 and detecting if binding has occurred.

4. A method for purifying γ-HRG comprising passing a mixture containing γ-HRG over a solid phase to which is bound the antibody of claim 1 and recovering the fraction containing γ-HRG.

* * * * *